(12) United States Patent
Teng

(10) Patent No.: US 12,187,754 B2
(45) Date of Patent: Jan. 7, 2025

(54) LPXC INHIBITORS AND USES THEREOF

(71) Applicant: Blacksmith Medicines, Inc., San Diego, CA (US)

(72) Inventor: Min Teng, San Diego, CA (US)

(73) Assignee: BLACKSMITH MEDICINES, INC., San Diego, CA (US)

( * ) Notice: Subject to any disclaimer, the term of this patent is extended or adjusted under 35 U.S.C. 154(b) by 0 days.

(21) Appl. No.: 18/616,636

(22) Filed: Mar. 26, 2024

(65) Prior Publication Data

US 2024/0270773 A1    Aug. 15, 2024

Related U.S. Application Data

(63) Continuation of application No. PCT/US2022/044710, filed on Sep. 26, 2022.

(60) Provisional application No. 63/249,166, filed on Sep. 28, 2021.

(51) Int. Cl.
| A61K 31/675 | (2006.01) |
| A61P 13/02 | (2006.01) |
| A61P 31/04 | (2006.01) |
| C07F 9/6558 | (2006.01) |

(52) U.S. Cl.
CPC ........ *C07F 9/65583* (2013.01); *A61K 31/675* (2013.01); *A61P 13/02* (2018.01); *A61P 31/04* (2018.01)

(58) Field of Classification Search
CPC .................................................. A61K 31/675
See application file for complete search history.

(56) References Cited

U.S. PATENT DOCUMENTS

| 5,543,534 | A | 8/1996 | Vuligonda et al. |
| 5,846,514 | A | 12/1998 | Foster et al. |
| 6,334,997 | B1 | 1/2002 | Foster et al. |
| 6,699,849 | B1 | 3/2004 | Loftsson et al. |
| 7,211,572 | B2 | 5/2007 | Miyazaki et al. |
| 7,579,486 | B2 | 8/2009 | Puerta et al. |
| 7,786,316 | B2 | 8/2010 | Puerta et al. |
| 9,145,381 | B2 | 9/2015 | Fanelli et al. |
| 10,130,714 | B2 | 11/2018 | Wong et al. |
| 10,414,735 | B2 | 9/2019 | Teng et al. |
| 10,611,747 | B2 | 4/2020 | Teng et al. |
| 10,875,832 | B2 | 12/2020 | Teng et al. |
| 11,021,471 | B2 | 6/2021 | Teng et al. |
| 11,407,740 | B2 * | 8/2022 | Teng ............... C07D 401/12 |
| 11,731,962 | B2 | 8/2023 | Teng et al. |
| 2003/0181472 | A1 | 9/2003 | Clark et al. |
| 2003/0190608 | A1 | 10/2003 | Blackburn |
| 2005/0009101 | A1 | 1/2005 | Blackburn |
| 2007/0117848 | A1 | 5/2007 | Puerta et al. |
| 2007/0149556 | A1 | 6/2007 | Mikamiyama et al. |
| 2008/0317851 | A1 | 12/2008 | Appel et al. |
| 2012/0035255 | A1 | 2/2012 | Fanelli et al. |
| 2012/0041032 | A1 | 2/2012 | Puerta et al. |
| 2012/0329741 | A1 | 12/2012 | Oyelere et al. |
| 2014/0038990 | A1 | 2/2014 | Buschmann et al. |
| 2014/0079666 | A1 | 3/2014 | Webb et al. |
| 2015/0202208 | A1 | 7/2015 | Kiyama et al. |
| 2017/0088532 | A1 | 3/2017 | Cohen et al. |
| 2017/0290918 | A1 | 10/2017 | Honda et al. |
| 2018/0327365 | A1 | 11/2018 | Teng et al. |
| 2019/0106398 | A1 | 4/2019 | Cohen et al. |
| 2020/0062789 | A1 | 2/2020 | Shoji et al. |
| 2020/0095236 | A1 | 3/2020 | Teng et al. |
| 2021/0078957 | A1 | 3/2021 | Teng et al. |
| 2021/0221796 | A1 | 7/2021 | Teng et al. |
| 2021/0315902 | A1 | 10/2021 | Teng et al. |
| 2022/0324846 | A1 | 10/2022 | Teng et al. |
| 2023/0201214 | A1 | 6/2023 | Teng et al. |
| 2023/0382891 | A1 | 11/2023 | Teng et al. |
| 2024/0002373 | A1 | 1/2024 | Teng et al. |

FOREIGN PATENT DOCUMENTS

| CN | 105777464 A | 7/2016 |
| EP | 2181985 B1 | 10/2011 |
| WO | WO-9830205 A1 | 7/1998 |
| WO | WO-2004062601 A2 | 7/2004 |
| WO | WO-2005110399 A2 | 11/2005 |
| WO | WO-2006028523 A2 | 3/2006 |
| WO | WO-2008027466 A1 | 3/2008 |
| WO | WO-2008045668 A1 | 4/2008 |
| WO | WO-2008154642 A2 | 12/2008 |
| WO | WO-2010059838 A2 | 5/2010 |
| WO | WO-2010100475 A1 | 9/2010 |
| WO | WO-2012151567 A1 | 11/2012 |

(Continued)

OTHER PUBLICATIONS

Aytemir et al. Synthesis and Evaluation of Anticonvulsant and Antimicrobial Activities of 3-Hydroxy-6-methyl-2-substituted 4H-Pyran-4-one Derivatives. Archiv Der Pharmazie 337(5):281-288 (2004).
Banker et al. Modern Pharmaceutics. 3rd ed. Marcel Dekker, New York.p. 596 (1996).
Barb et al. Mechanism and inhibition of LpxC: an essential zinc-dependent deacetylase of bacterial lipid A synthesis. Curr Pharm Biotechnol 9(1):9-15 (2008).
Berge et al., Pharmaceutical Salts. Journal of Pharmaceutical Sciences 66(1):1-19 (1977).
Bingi et al. One-pot catalyst free synthesis of novel kojic acid tagged 2-aryl/alkyl substituted-4H-chromenes and evaluation of their antimicrobial and anti-biofilm activities. Bioorganic & Medicinal Chemistry Letters 25(9):1915-1919 (2015).
Bundgaard et al. Design of Prodrugs pp. 7-9, 21-24 (1985).

(Continued)

*Primary Examiner* — Rei Tsang Shiao
(74) *Attorney, Agent, or Firm* — WILSON SONSINI GOODRICH & ROSATI

(57) ABSTRACT

Provided herein are LpxC inhibitor compounds, as well as pharmaceutical compositions comprising said compounds, and methods of use thereof in the treatment of disease that would benefit from treatment with an LpxC inhibitor, including gram-negative bacterial infections such as urinary tract infections and the like.

4 Claims, 2 Drawing Sheets

(56) References Cited

FOREIGN PATENT DOCUMENTS

| | | |
|---|---|---|
| WO | WO-2012177638 A1 | 12/2012 |
| WO | WO-2013151923 A1 | 10/2013 |
| WO | WO-2014117090 A1 | 7/2014 |
| WO | WO-2014160649 A1 | 10/2014 |
| WO | WO-2015024010 A2 | 2/2015 |
| WO | WO-2015085238 A1 | 6/2015 |
| WO | WO-2015099107 A1 | 7/2015 |
| WO | WO-2017083431 A2 | 5/2017 |
| WO | WO-2017083434 A1 | 5/2017 |
| WO | WO-2018115421 A1 | 6/2018 |
| WO | WO-2018208985 A2 | 11/2018 |
| WO | WO-2018208987 A2 | 11/2018 |
| WO | WO-2019086452 A1 | 5/2019 |
| WO | WO-2019154412 A1 | 8/2019 |
| WO | WO-2020061375 A1 | 3/2020 |
| WO | WO-2020102572 A1 | 5/2020 |
| WO | WO-2021195258 A1 | 9/2021 |
| WO | WO-2021195260 A1 | 9/2021 |
| WO | WO-2022173758 A1 | 8/2022 |
| WO | WO-2023055686 A1 | 4/2023 |
| WO | WO-2024036170 A1 | 2/2024 |
| WO | WO-2024036176 A1 | 2/2024 |

OTHER PUBLICATIONS

Di Francesco et al. Development of 2-t butyl-N-methyl pyrimidones as potent inhibitors of HIV integrase. Bioorg Med Chem Lett 18(8):2709-13 (2008).
Ding et al. Design, synthesis and biological evaluation of LpxC inhibitors with novel hydrophilic terminus. Chinese Chemical Letters 26(6):763-767 (2015).
Emami et al. Mannich bases of 7-piperazinylquinolones and kojic acid derivatives: Synthesis, in vitro antibacterial activity and in silico study. Ep J Med Chem 68:185-191 (2010).
Evans.: Synthesis Of Radiolabelled Compounds. Journal of Radioanalytical and Nuclear Chemistry 64(1-2):9-32 (1981).
Garrett et al. The Art of Meeting Palladium Specifications in Active Pharmaceutical Ingredients Produced by Pd-Catalyzed Reactions. Adv. Synth. Catal. 346:889-900 (2004).
Guideline on the Specification Limits for Residues of Metal Catalysts. European Medicines Agency. Pre-authorization Evaluation of Medicines for Human Use, London (Jan. 2007) (pp. 1-32).
Hale et al. Exploring the UDP pocket of LpxC through amino acid analogs. Bioorg Med Chem Lett. 23:2362-2367 (2013).
Kabalka et al., The synthesis of radiolabeled compounds via organometallic intermediates. Tetrahedron 45(21):6601-6621 (1989).
Krivonogov et al. Aminomethylation of pyrimidines. Russian Journal of Organic Chemistry 36(8): 1219-1224 Chemical Abstracts CAS No. 345959-90-2P (2000).
Li et al. Design, synthesis and biological evaluation of 2-substituted 3-hydroxy-6-methyl-4H-pyran-4-one derivatives as Pseudomonas aeruginosa biofilm inhibitors. Eur J Med Chem 158:753-766 (2018).
Lin et al. Inhibition of LpxC protects mice from resistant Acinetobacter baumannii by modulating inflammation and enhancing phagocytosis. Mbio 3(5):pii:e00312-12 (2012).

Montgomery et al. Pyridone methylsulfone hydroxamate LpxC inhibitors for the treatment of serious gram-negative infections. J Med Chem 55:1662-1670 (2012).
PCT/US2016/061195 International Search Report and Written Opinion dated Jul. 31, 2017.
PCT/US2016/061198 International Search Report and Written Opinion dated Feb. 15, 2017.
PCT/US2018/031896 International Search Report and Written Opinion dated Nov. 7, 2018.
PCT/US2018/031898 International Search Report and Written Opinion dated Nov. 7, 2018.
PCT/US2019/051986 International Search Report and Written Opinion dated Jan. 3, 2020.
PCT/US2019/052021 International Search Report and Written Opinion dated Jan. 6, 2020.
PCT/US2019/061529 International Search Report and Written Opinion dated Mar. 13, 2020.
PCT/US2021/023948 International Search Report and Written Opinion dated Jun. 10, 2021.
PCT/US2021/023950 International Search Report and Written Opinion dated Jul. 28, 2021.
PCT/US2022/015679 International Search Report and Written Opinion dated May 31, 2022.
PCT/US2022/044710 International Search Report and Written Opinion dated Jan. 16, 2023.
Ravin. Chapter 76: Preformulation. Remington's Pharmaceutical Sciences, 17th ed., Mack Publishing Company, Easton, Pa. (pp. 1409-1423) (1985).
Storr et al., Vanadyl-thiazolidinedione combination agents for diabetes therapy. Bioconjugate Chemistry 14(1):212-221 (2003).
Us et al. 4H-Pyran-4-one derivatives:; leading molecule for preparation of compounds with antimycobacterial potential. Turkish Journal of Chemistry 30:803-812 (2009).
Us et al. Mannich base derivatives of 3-hydroxy-6- methyl-4H-pyran-4-one with antimicrobial activity. Turkish Journal of Chemistry 33:447-456 (2010).
U.S. Appl. No. 17/211,025 Office Action dated Sep. 26, 2022.
Ushiyama et al., Lead optimization of 2-hydroxymethyl imidazoles as non-hydroxamate LpxC inhibitors: Discovery of TP0586532. Bioorg Med Chem. 30:115964 (2021).
Vaara: Antibiotic-supersusceptible mutants of *Escherichia coli* and *Salmonella typhimurium*. Antimicrob Agents Chemother. 37(11):2255-2260 (1993).
Wolff, (ed.), Burger's Medicinal Chemistry and Drug Discovery, Fifth Edition, vol. 1: Principles and Practice, San Diego, California, John Wiley & Sons, 1994, pp. 975-977. (4 pages).
Wuts et al. Greene's Protective Groups in Organic Synthesis. 4th ed., Wiley & Sons (pp. 1-1082) (2007).
Yan et al. Synthesis of hydroxypyrone- and hydroxythiopyrone-based matrix metalloproteinase inhibitors: Developing a structure-activity relationship. Bioorg. Med. Chem. Lett. 19(7):1970-1976 (2009).
Young et al.: Leakage of periplasmic enzymes from envA1 strains of *Escherichia coli*. J. Bacteriol.173(12):3609-3614 (1991).

* cited by examiner

LPXC INHIBITORS AND USES THEREOF

CROSS-REFERENCE

This application is a continuation of International Application No. PCT/US2022/044710, filed Sep. 26, 2022, which claims benefit of U.S. Provisional Patent Application No. 63/249,166, filed on Sep. 28, 2021, all of which are incorporated herein by reference in their entirety.

BACKGROUND

A need exists in the medicinal arts for the effective treatment of illness caused by bacterial infection.

BRIEF SUMMARY OF THE INVENTION

Provided herein are LpxC inhibitor compounds, as well as pharmaceutical compositions comprising said compound, and methods of use thereof in the treatment of disease that would benefit from treatment with an LpxC inhibitor, including gram-negative bacterial infections such as urinary tract infections and the like.

In one aspect, provided herein is a compound having the structure of Formula (I):

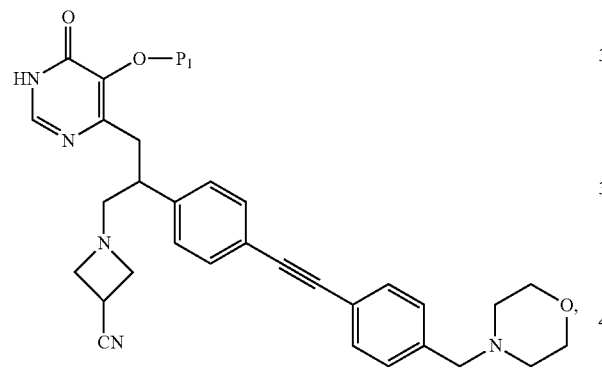

Formula (I)

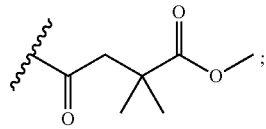 [SMILES: *C(=O)CC(C)(C)C(=O)OC]

or a pharmaceutically acceptable salt, or a pharmaceutically acceptable solvate thereof, wherein:

$P_1$ is —P(=O)(OR$^1$)$_2$, —(CR$^3$R$^4$)—O—P(=O)(OR$^1$)$_2$, —S(=O)$_2$OR$^1$, —(CR$^3$R$^4$)—O—S(=O)$_2$OR$^1$, —S(=O)$_2$R$^2$, —(CR$^3$R$^4$)—O—S(=O)$_2$R$^2$, —C(=O)R$^2$, —(CR$^3$R$^4$)—O—C(=O)R$^2$, —C(=O)OR$^2$, —(CR$^3$R$^4$)—O—C(=O)OR$^2$, —C(=O)—O—(CR$^3$R$^4$)—O—C(=O)R$^2$, —C(=O)NR$^5$R$^6$, or each $R^1$ is independently hydrogen, $C_1$-$C_4$ alkyl, $C_3$-$C_6$ cycloalkyl, 4- to 6-membered heterocycloalkyl, phenyl, or monocyclic heteroaryl;

$R^2$ is $C_1$-$C_4$ alkyl, $C_3$-$C_6$ cycloalkyl, 4- to 6-membered heterocycloalkyl, phenyl, or monocyclic heteroaryl;

$R^3$ and $R^4$ are each independently hydrogen, $C_1$-$C_4$ alkyl, $C_3$-$C_6$ cycloalkyl, 4- to 6-membered heterocycloalkyl, phenyl, or monocyclic heteroaryl;

$R^5$ and $R^6$ are each independently hydrogen, $C_1$-$C_4$ alkyl, $C_3$-$C_6$ cycloalkyl, 4- to 6-membered heterocycloalkyl, phenyl, or monocyclic heteroaryl;

or $R^5$ and $R^6$ are taken together with the nitrogen atom to which they are attached to form a 4- to 6-membered heterocycloalkyl which is unsubstituted or is substituted with 1, 2, or 3 substituents selected from the group consisting of $C_1$-$C_4$ alkyl, $C_1$-$C_4$ fluoroalkyl, $C_3$-$C_6$ cycloalkyl, and 4- to 6-membered heterocycloalkyl.

In some embodiments, the compound has the structure of Formula (Ia):

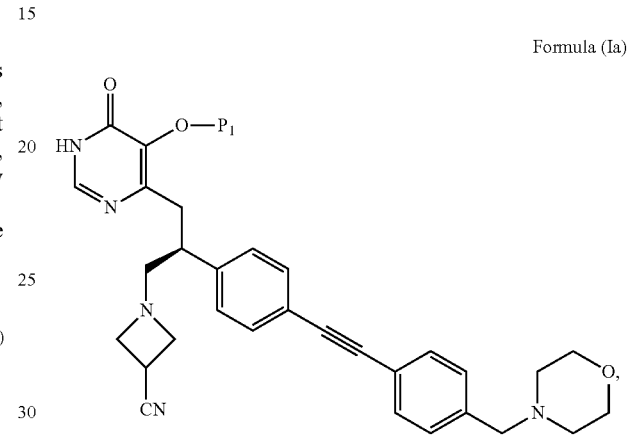

Formula (Ia)

or a pharmaceutically acceptable salt, or a pharmaceutically acceptable solvate thereof.

In some embodiments, the compound has the structure of Formula (Ib):

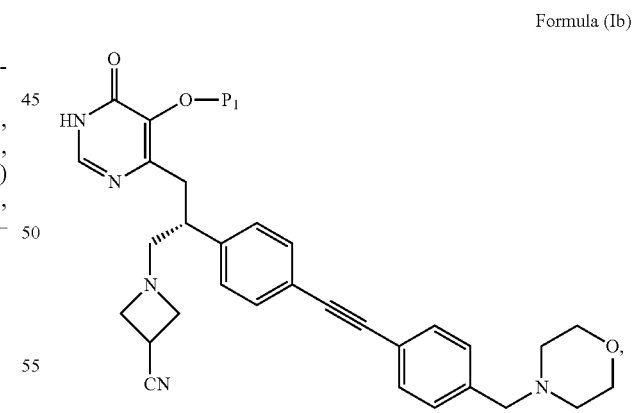

Formula (Ib)

or a pharmaceutically acceptable salt, or a pharmaceutically acceptable solvate thereof.

In some embodiments, $P_1$ is —P(=O)(OR$^1$)$_2$, —CH$_2$—O—P(=O)(OR$^1$)$_2$, —S(=O)$_2$OR$^1$, —S(=O)$_2$R$^2$, —C(=O)OR$^2$, —(CHR$^4$)—O—C(=O)OR$^2$, —C(=O)—O—(CHR$^4$)—O—C(=O)R$^2$, —C(=O)R$^2$, —CH$_2$—O—C(=O)R$^2$, —C(=O)NR$^5$R$^6$, or

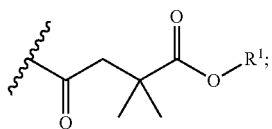

each $R^1$ is independently hydrogen, $C_1$-$C_4$ alkyl, $C_3$-$C_6$ cycloalkyl, or phenyl;
$R^2$ is $C_1$-$C_4$ alkyl, $C_3$-$C_6$ cycloalkyl, or phenyl;
$R^4$ is hydrogen, $C_1$-$C_4$ alkyl, $C_3$-$C_6$ cycloalkyl, or phenyl; and
$R^5$ and $R^6$ are each independently hydrogen, $C_1$-$C_4$ alkyl, $C_3$-$C_6$ cycloalkyl, or phenyl;
or $R^5$ and $R^6$ are taken together with the nitrogen atom to which they are attached to form a 4- to 6-membered heterocycloalkyl which is unsubstituted or is substituted with 1 or 2 substituents selected from the group consisting of $C_1$-$C_4$ alkyl and 4- to 6-membered heterocycloalkyl.

In some embodiments,
each $R^1$ is independently hydrogen, —$CH_3$, —$CH_2CH_3$, or —$CH(CH_3)_2$;
$R^2$ is —$CH_3$, —$CH_2CH_3$, —$CH(CH_3)_2$, or $C(CH_3)_3$;
$R^4$ is hydrogen, —$CH_3$, or phenyl; and
$R^5$ and $R^6$ are each independently hydrogen, —$CH_3$, or —$CH_2CH_3$;
or $R^5$ and $R^6$ are taken together with the nitrogen atom to which they are attached to form a 4- to 6-membered heterocycloalkyl which is unsubstituted or is substituted with 1 or 2 substituents selected from the group consisting of $C_1$-$C_4$ alkyl and 4- to 6-membered heterocycloalkyl.

In some embodiments, $P_1$ is —P(=O)(OH)$_2$, —CH$_2$—O—P(=O)(OH)$_2$, —S(=O)$_2$OH, —S(=O)$_2$CH$_3$, —C(=O)OCH$_2$CH$_3$, —(CH(CH$_3$))—O—C(=O)OCH(CH$_3$)$_2$, —(CH(CH$_3$))—O—C(=O)OCH$_2$CH$_3$, —C(=O)—O—(CH(phenyl))-O—C(=O)C(CH$_3$)$_3$, —C(=O)C(CH$_3$)$_3$, —CH$_2$—O—C(=O)C(CH$_3$)$_3$, —C(=O)N(CH$_3$)$_2$, or

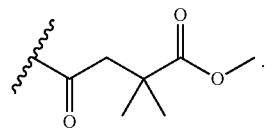 [SMILES: *C(=O)CC(C)(C)C(=O)OC]

In another aspect, disclosed herein are pharmaceutical compositions comprising a compound described herein, or a pharmaceutically acceptable salt, or a pharmaceutically acceptable solvate thereof, and at least one pharmaceutically acceptable excipient. In some embodiments, the pharmaceutical compositions are formulated for administration to a mammal by intravenous administration or oral administration. In some embodiments, the pharmaceutical compositions are in the form of a tablet, a pill, a capsule, a liquid, a suspension, a dispersion, or a solution.

In another aspect, disclosed herein is a method of treating a gram-negative bacterial infection in a patient in need thereof comprising administering to the patient a compound disclosed herein, or a pharmaceutically acceptable salt, or a pharmaceutically acceptable solvate thereof. In some embodiments, the gram-negative bacterial infection is selected from pneumonia, sepsis, cystic fibrosis, intra-abdominal infection, skin infection and urinary tract infection. In some embodiments, the gram-negative bacterial infection is selected from chronic urinary tract infection, complicated urinary tract infection, cystitis, pyelonephritis, urethritis, recurrent urinary tract infections, bladder infections, urethral infections and kidney infections. In some embodiments, the gram-negative bacterial infection is chronic urinary tract infections. In some embodiments, the gram-negative bacterial infection is complicated urinary tract infections. In some embodiments, the compound has no effect on gram-positive bacteria.

In some embodiments, the compound disclosed herein, or a pharmaceutically acceptable salt, or a pharmaceutically acceptable solvate thereof, is administered to the patient by I.V. injection or infusion. In other embodiments, the compound disclosed herein, or a pharmaceutically acceptable salt, or a pharmaceutically acceptable solvate thereof, is administered to the patient orally.

In some embodiments, the administration is to treat an existing infection. In other embodiments, the administration is provided as prophylaxis.

Articles of manufacture, which include packaging material, the LpxC inhibitory compounds described herein, or a pharmaceutically acceptable salt, or a pharmaceutically acceptable solvate thereof, within the packaging material, and a label that indicates that the compound or a pharmaceutically acceptable salt, or a pharmaceutically acceptable solvate thereof, or composition thereof, is used for modulating the activity of LpxC, or for the treatment, prevention or amelioration of one or more symptoms of a disease or condition that would benefit from modulation of LpxC activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference for the specific purposes identified herein.

DETAILED DESCRIPTION OF THE INVENTION

Figure 1:
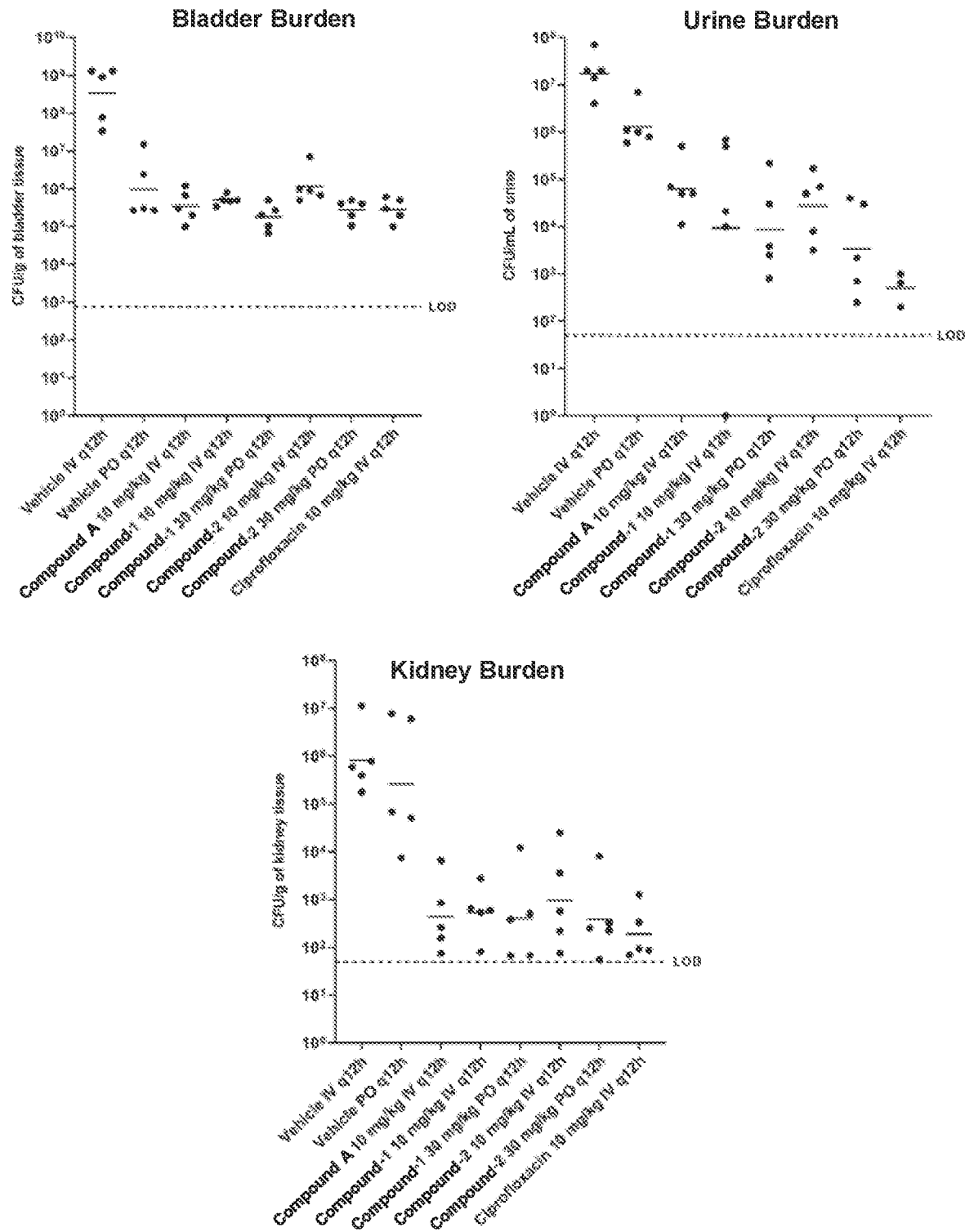
FIG. 1 shows the average terminal burden of *E. coli* UTI 89 in urine, bladder, and kidney at the conclusion of a 96 h urinary tract infection study.

Provided herein are LpxC inhibitor compounds, as well as pharmaceutical compositions comprising said compound, and methods of use thereof in the treatment of disease that would benefit from treatment with an LpxC inhibitor, including gram-negative bacterial infections such as urinary tract infections and the like. In some embodiments, the compounds provided herein are prodrugs of Compound A.

Compound A

Compound A refers to (S)-1-(3-(5-hydroxy-6-oxo-1,6-dihydropyrimidin-4-yl)-2-(4-((4-(morpholinomethyl)phenyl)ethynyl)phenyl)propyl)azetidine-3-carbonitrile which has the chemical structure shown below.

(Compound A)

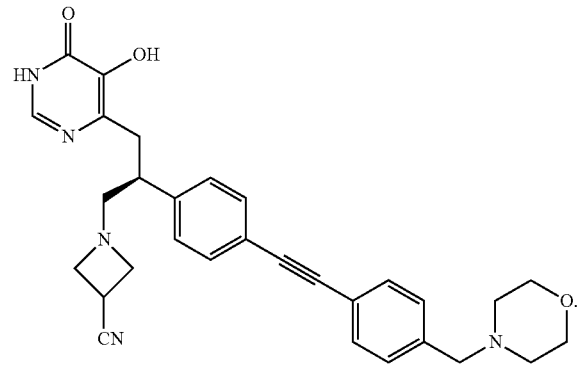

Compound A is also known as (S)-1-(3-(5,6-dihydroxypyrimidin-4-yl)-2-(4-((4-(morpholinomethyl)phenyl)ethynyl)phenyl)propyl)azetidine-3-carbonitrile, which is a tautomer of the above structure and has the chemical structure shown below.

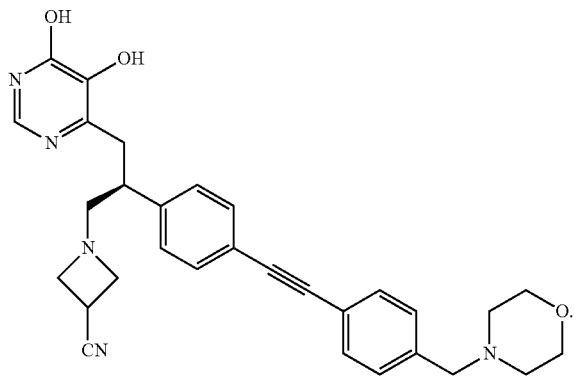 [SMILES: N#CC1CN(C[C@@H](Cc2ncnc(O)c2O)c2ccc(C#Cc3ccc(CN4CCOCC4)cc3)cc2)C1]

Compound A is a potent inhibitor of UDP-{3-O—[(R)-3-hydroxymyristoyl]}-N-acetylglucosamine deacetylase (LpxC). LpxC is an essential enzyme involved in the first committed step in lipid A biosynthesis for gram-negative bacteria. Lipid A is an essential component of the outer membrane of gram-negative bacteria. LpxC is highly conserved across strains of gram-negative bacteria, making LpxC an attractive target to treat gram-negative infections.

Compound A is an LpxC inhibitor that is useful in the methods of treatment described herein. In gram-negative bacterial cell lines, Compound A is a potent inhibitor, exhibiting MIC values of <1 µg/mL against *E. coli* and *K. pneumoniae* cell lines. Additionally, Compound A does not inhibit gram-positive bacterial cell lines, such as *S. aureus*.

The preparation and use of Compound A has been previously described (see, WO 2020/061375, US 2021/0221796, WO 2021/195260, and US 2021/0309651 each of which is incorporated by reference in its entirety).

Prodrugs

The term "prodrug" is meant to indicate a compound that is, in some embodiments, converted under physiological conditions or by solvolysis to a biologically active compound. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7 9, 21 24 (Elsevier, Amsterdam). A discussion of prodrugs is provided in Higuchi, T., et al., "Prodrugs as Novel Delivery Systems," A.C.S. Symposium Series, Vol. 14, and in Bioreversible Carriers in Drug Design, ed. Edward B. Roche, American Pharmaceutical Association and Pergamon Press, 1987. The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate, benzoate, phosphate, sulfonate, carbonate, and carbamate derivatives of alcohol or amine functional groups in the active compounds and the like.

In some aspects, disclosed herein is a prodrug of Compound A:

(Compound A)

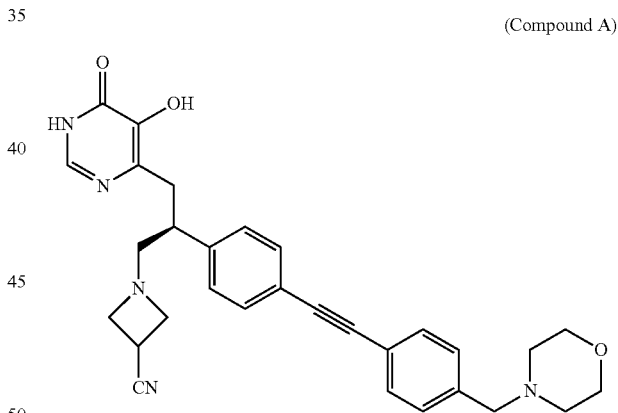

or a pharmaceutically acceptable salt, or a pharmaceutically acceptable solvate thereof, wherein: the prodrug group is attached to a hydroxy or amino group of Compound A; and wherein the prodrug moiety comprises a phosphate, sulfonate, sulfate, ester, carbonate, or carbamate group.

In some embodiments, the prodrug is attached to a hydroxy group of Compound A. In some embodiments, the prodrug is attached to an amino group of Compound A.

In some embodiments the prodrug moiety comprises a phosphate group. In some embodiments the prodrug moiety comprises a sulfonate group. In some embodiments the prodrug moiety comprises a sulfate group. In some embodiments the prodrug moiety comprises an ester group. In some embodiments the prodrug moiety comprises a carbonate group. In some embodiments the prodrug moiety comprises a carbamate group.

While Compound A is highly active in in vitro cell based assays, in some instances its low physiological solubility leads to challenges using it in vivo. In some embodiments, the solubility of Compound A is increased by using a prodrug of Compound A. In some embodiments, a prodrug of Compound A provided herein, for example, a phosphate prodrug, has a 2-fold, 3-fold, 4-fold, 5-fold, 6-fold, 7-fold, 8-fold, 9-fold, 10-fold, or more than 10-fold increase in solubility relative to Compound A under physiological conditions. In some embodiments, the solubility of Compound A under physiological conditions, for example at pH 7.4, is <1 mg/mL. In some embodiments, the solubility of a prodrug of Compound A provided herein, for example, a phosphate prodrug, is >10 mg/mL under the same physiological conditions.

Compounds

In another aspect, provided herein is a compound having the structure of Formula (I):

Formula (I)

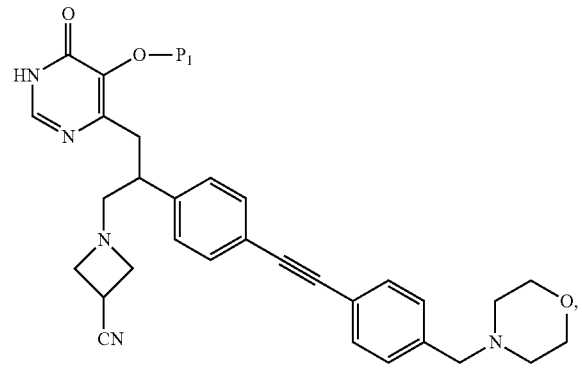

or a pharmaceutically acceptable salt, or a pharmaceutically acceptable solvate thereof, wherein:

$P_1$ is —P(=O)(OR$^1$)$_2$, —(CR$^3$R$^4$)—O—P(=O)(OR$^1$)$_2$, —S(=O)$_2$OR$^1$, —(CR$^3$R$^4$)—O—S(=O)$_2$OR$^1$, —S(=O)$_2$R$^2$, —(CR$^3$R$^4$)—O—S(=O)$_2$R$^2$, —C(=O)R$^2$, —(CR$^3$R$^4$)—O—C(=O)R$^2$, —C(=O)OR$^2$, —(CR$^3$R$^4$)—O—C(=O)OR$^2$, —C(=O)—O—(CR$^3$R$^4$)—O—C(=O)R$^2$, —C(=O)NR$^5$R$^6$, or

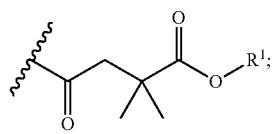

each R$^1$ is independently hydrogen, C$_1$-C$_4$ alkyl, C$_3$-C$_6$ cycloalkyl, 4- to 6-membered heterocycloalkyl, phenyl, or monocyclic heteroaryl;

R$^2$ is C$_1$-C$_4$ alkyl, C$_3$-C$_6$ cycloalkyl, 4- to 6-membered heterocycloalkyl, phenyl, or monocyclic heteroaryl;

R$^3$ and R$^4$ are each independently hydrogen, C$_1$-C$_4$ alkyl, C$_3$-C$_6$ cycloalkyl, 4- to 6-membered heterocycloalkyl, phenyl, or monocyclic heteroaryl;

R$^5$ and R$^6$ are each independently hydrogen, C$_1$-C$_4$ alkyl, C$_3$-C$_6$ cycloalkyl, 4- to 6-membered heterocycloalkyl, phenyl, or monocyclic heteroaryl;

or R$^5$ and R$^6$ are taken together with the nitrogen atom to which they are attached to form a 4- to 6-membered heterocycloalkyl which is unsubstituted or is substituted with 1, 2, or 3 substituents selected from the group consisting of C$_1$-C$_4$ alkyl, C$_1$-C$_4$ fluoroalkyl, C$_3$-C$_6$ cycloalkyl, and 4- to 6-membered heterocycloalkyl.

In some embodiments, the compound has the structure of Formula (Ia):

Formula (Ia)

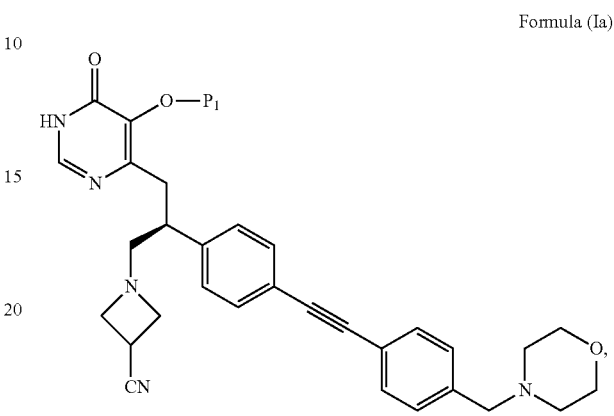

or a pharmaceutically acceptable salt, or a pharmaceutically acceptable solvate thereof.

In some embodiments, the compound has the structure of Formula (Ib):

Formula (Ib)

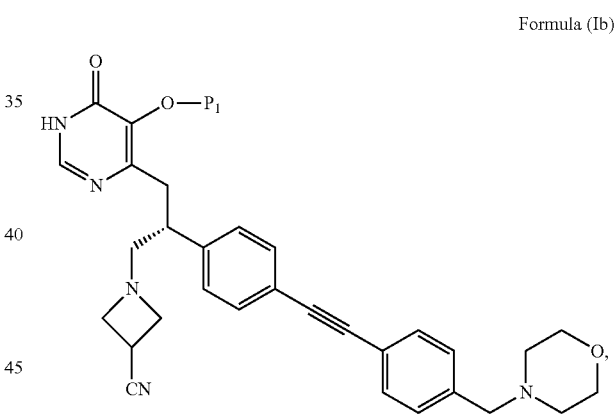

or a pharmaceutically acceptable salt, or a pharmaceutically acceptable solvate thereof.

For any and all of the embodiments, substituents are selected from among a subset of the listed alternatives. For example, in some embodiments, R$^3$ is hydrogen, C$_1$-C$_4$ alkyl, C$_3$-C$_6$ cycloalkyl, or phenyl. In some embodiments, R$^3$ is hydrogen, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, cyclopropyl, cyclobutyl, cyclopentyl, cyclohexyl, or phenyl. In some embodiments, R$^3$ is hydrogen, —CH$_3$, or phenyl. In some embodiments, R$^3$ is hydrogen or C$_1$-C$_4$ alkyl. In some embodiments, R$^3$ is hydrogen, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), or —C(CH$_3$)$_3$. In some embodiments, R$^3$ is hydrogen or —CH$_3$. In some embodiments, R$^3$ is hydrogen.

In some embodiments, R$^4$ is hydrogen, C$_1$-C$_4$ alkyl, C$_3$-C$_6$ cycloalkyl, or phenyl. In some embodiments, R$^4$ is hydrogen, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, cyclopropyl, cyclobutyl, cyclopentyl, cyclohexyl, or phenyl. In some embodiments, R$^4$ is hydrogen, —CH$_3$, or phenyl. In some embodiments, R$^4$ is hydrogen or C$_1$-C$_4$ alkyl. In some embodiments, R$^4$ is hydrogen, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), or —C(CH$_3$)$_3$. In some embodiments, R$^4$ is hydrogen or —CH$_3$. In some embodiments, R$^4$ is hydrogen.

In some embodiments, R$^3$ and R$^4$ are each independently hydrogen, C$_1$-C$_4$ alkyl, C$_3$-C$_6$ cycloalkyl, or phenyl. In some embodiments, R$^3$ and R$^4$ are each independently hydrogen, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, cyclopropyl, cyclobutyl, cyclopentyl, cyclohexyl, or phenyl. In some embodiments, R$^3$ and R$^4$ are each independently hydrogen, —CH$_3$, or phenyl. In some embodiments, R$^3$ and R$^4$ are each independently hydrogen or C$_1$-C$_4$ alkyl. In some embodiments, R$^3$ and R$^4$ are each independently hydrogen, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), or —C(CH$_3$)$_3$. In some embodiments, R$^3$ and R$^4$ are each independently hydrogen or —CH$_3$. In some embodiments, R$^3$ and R$^4$ are each hydrogen.

In some embodiments, each R$^1$ is independently hydrogen, C$_1$-C$_4$ alkyl, C$_3$-C$_6$ cycloalkyl, or phenyl. In some embodiments, each R$^1$ is independently hydrogen or C$_1$-C$_4$ alkyl. In some embodiments, each R$^1$ is independently hydrogen, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), or —C(CH$_3$)$_3$. In some embodiments, each R$^1$ is independently hydrogen, —CH$_3$, —CH$_2$CH$_3$, or —CH(CH$_3$)$_2$. In some embodiments, each R$^1$ is hydrogen.

In some embodiments, R$^2$ is C$_1$-C$_4$ alkyl, C$_3$-C$_6$ cycloalkyl, or phenyl. In some embodiments, R$^2$ is C$_1$-C$_4$ alkyl. In some embodiments, R$^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), or —C(CH$_3$)$_3$. In some embodiments, R$^2$ is —CH$_3$, —CH$_2$CH$_3$, —CH(CH$_3$)$_2$, or —C(CH$_3$)$_3$.

In some embodiments, P$_1$ is —P(=O)(OR$^1$)$_2$ or —(CR$^3$R$^4$)—O—P(=O)(OR$^1$)$_2$. In some embodiments, P$_1$ is —P(=O)(OR$^1$)$_2$ or —(CR$^3$R$^4$)—O—P(=O)(OR$^1$)$_2$; each R$^1$ is independently hydrogen or C$_1$-C$_4$ alkyl; and R$^3$ and R$^4$ are each independently hydrogen, C$_1$-C$_4$ alkyl, or C$_3$-C$_6$ cycloalkyl. In some embodiments, P$_1$ is —P(=O)(OR$^1$)$_2$ or —CH$_2$—O—P(=O)(OR$^1$)$_2$; and each R$^1$ is independently hydrogen, —CH$_3$, —CH$_2$CH$_3$, or —CH(CH$_3$)$_2$. In some embodiments, P$_1$ is —P(=O)(OH)$_2$ or —CH$_2$—O—P(=O)(OH)$_2$.

In some embodiments, P$_1$ is —P(=O)(OR$^1$)$_2$. In some embodiments, P$_1$ is —P(=O)(OR$^1$)$_2$; and each R$^1$ is independently hydrogen or C$_1$-C$_4$ alkyl. In some embodiments, P$_1$ is —P(=O)(OR$^1$)$_2$; and each R$^1$ is independently hydrogen, —CH$_3$, —CH$_2$CH$_3$, or —CH(CH$_3$)$_2$. In some embodiments, P$_1$ is —P(=O)(OH)$_2$.

In some embodiments, P$_1$ is —(CR$^3$R$^4$)—O—P(=O)(OR$^1$)$_2$. In some embodiments, P$_1$ is —(CR$^3$R$^4$)—O—P(=O)(OR$^1$)$_2$; each R$^1$ is independently hydrogen or C$_1$-C$_4$ alkyl; and R$^3$ and R$^4$ are each independently hydrogen, C$_1$-C$_4$ alkyl, or C$_3$-C$_6$ cycloalkyl. In some embodiments, P$_1$ is —CH$_2$—O—P(=O)(OR$^1$)$_2$; and each R$^1$ is independently hydrogen, —CH$_3$, —CH$_2$CH$_3$, or —CH(CH$_3$)$_2$. In some embodiments, P$_1$ is —CH$_2$—O—P(=O)(OH)$_2$.

In some embodiments, P$_1$ is —S(=O)$_2$OR$^1$ or —(CR$^3$R$^4$)—O—S(=O)$_2$OR$^1$. In some embodiments, P$_1$ is —S(=O)$_2$OR$^1$ or —(CR$^3$R$^4$)—O—S(=O)$_2$OR$^1$; R$^1$ is hydrogen or C$_1$-C$_4$ alkyl; and R$^3$ and R$^4$ are each independently hydrogen, C$_1$-C$_4$ alkyl, or C$_3$-C$_6$ cycloalkyl. In some embodiments, P$_1$ is —S(=O)$_2$OR$^1$. In some embodiments, P$_1$ is —(CR$^3$R$^4$)—O—S(=O)$_2$OR$^1$. In some embodiments, P$_1$ is —S(=O)$_2$OR$^1$; and R$^1$ is hydrogen, —CH$_3$, —CH$_2$CH$_3$, or —CH(CH$_3$)$_2$. In some embodiments, P$_1$ is —S(=O)$_2$OH.

In some embodiments, P$_1$ is —S(=O)$_2$R$^2$ or —(CR$^3$R$^4$)—O—S(=O)$_2$R$^2$. In some embodiments, P$_1$ is —S(=O)$_2$R$^2$ or —(CR$^3$R$^4$)—O—S(=O)$_2$R$^2$; R$^2$ is C$_1$-C$_4$ alkyl; and R$^3$ and R$^4$ are each independently hydrogen, C$_1$-C$_4$ alkyl, C$_3$-C$_6$ cycloalkyl. In some embodiments, P$_1$ is —S(=O)$_2$R$^2$ or —(CR$^3$R$^4$)—O—S(=O)$_2$R$^2$; R$^2$ is C$_1$-C$_4$ alkyl; and R$^3$ and R$^4$ are each independently hydrogen, C$_1$-C$_4$ alkyl, C$_3$-C$_6$ cycloalkyl. In some embodiments, P$_1$ is —S(=O)$_2$R$^2$. In some embodiments, P$_1$ is —(CR$^3$R$^4$)—O—S(=O)$_2$R$^2$. In some embodiments, P$_1$ is —S(=O)$_2$R$^2$; and R$^2$ is —CH$_3$, —CH$_2$CH$_3$, or —CH(CH$_3$)$_2$. In some embodiments, P$_1$ is —S(=O)$_2$CH$_3$.

In some embodiments, P$_1$ is —C(=O)OR$^2$, —(CR$^3$R$^4$)—O—C(=O)OR$^2$, or —C(=O)—O—(CR$^3$R$^4$)—O—C(=O)R$^2$. In some embodiments, P$_1$ is —C(=O)OR$^2$, —(CR$^3$R$^4$)—O—C(=O)OR$^2$, or —C(=O)—O—(CR$^3$R$^4$)—O—C(=O)R$^2$; R$^2$ is C$_1$-C$_4$ alkyl; and R$^3$ and R$^4$ are each independently hydrogen, C$_1$-C$_4$ alkyl, C$_3$-C$_6$ cycloalkyl, or phenyl. In some embodiments, P$_1$ is —C(=O)OR$^2$, —(CHR$^4$)—O—C(=O)OR$^2$, or —C(=O)—O—(CHR$^4$)—O—C(=O)R$^2$; R$^2$ is —CH$_3$, —CH$_2$CH$_3$, or —CH(CH$_3$)$_2$; and R$^4$ is hydrogen, —CH$_3$, or phenyl. In some embodiments, P$_1$ is —C(=O)OR$^2$. In some embodiments, P$_1$ is —(CR$^3$R$^4$)—O—C(=O)OR$^2$. In some embodiments, P$_1$ is —C(=O)—O—(CR$^3$R$^4$)—O—C(=O)R$^2$.

In some embodiments, P$_1$ is —C(=O)R$^2$ or —(CR$^3$R$^4$)—O—C(=O)R$^2$. In some embodiments, P$_1$ is —C(=O)R$^2$ or —(CR$^3$R$^4$)—O—C(=O)R$^2$; R$^2$ is C$_1$-C$_4$ alkyl; and R$^3$ and R$^4$ are each independently hydrogen, C$_1$-C$_4$ alkyl, C$_3$-C$_6$ cycloalkyl, or phenyl. In some embodiments, P$_1$ is —C(=O)R$^2$ or —CH$_2$—O—C(=O)R$^2$; R$^2$ is —CH$_3$, —CH$_2$CH$_3$, —CH(CH$_3$)$_2$, or C(CH$_3$)$_3$. In some embodiments, P$_1$ is —C(=O)R$^2$. In some embodiments, P$_1$ is —(CR$^3$R$^4$)—O—C(=O)R$^2$.

In some embodiments, P$_1$ is —C(=O)NR$^5$R$^6$. In some embodiments, R$^5$ and R$^6$ are each independently hydrogen, C$_1$-C$_4$ alkyl, or C$_3$-C$_6$ cycloalkyl. In some embodiments, R$^5$ and R$^6$ are each independently hydrogen or C$_1$-C$_4$ alkyl. In some embodiments, R$^5$ and R$^6$ are each independently hydrogen, —CH$_3$, or —CH$_2$CH$_3$. In some embodiments, R$^5$ and R$^6$ are taken together with the nitrogen atom to which they are attached to form a 4- to 6-membered heterocycloalkyl which is unsubstituted or is substituted with 1 or 2 substituents selected from the group consisting of C$_1$-C$_4$ alkyl and 4- to 6-membered heterocycloalkyl.

In some embodiments, P$_1$ is

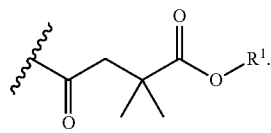

In some embodiments, $P_1$ is

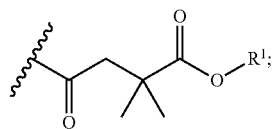

and $R^1$ is hydrogen or $C_1$-$C_4$ alkyl. In some embodiments, $P_1$ is

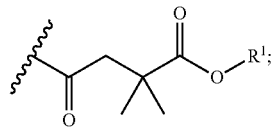

and $R^1$ is hydrogen, —$CH_3$, —$CH_2CH_3$, or —$CH(CH_3)_2$. In some embodiments, $P_1$ is

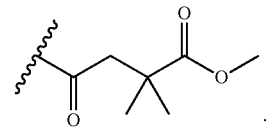 [SMILES: *C(=O)CC(C)(C)C(=O)OC]

In some embodiments,
$P_1$ is —P(=O)(OR$^1$)$_2$, —CH$_2$—O—P(=O)(OR$^1$)$_2$, —S(=O)$_2$OR$^1$, —S(=O)$_2$R$^2$, —C(=O)OR$^2$, —(CHR$^4$)—O—C(=O)OR$^2$, —C(=O)—O—(CHR$^4$)—O—C(=O)R$^2$, —C(=O)R$^2$, —CH$_2$—O—C(=O)R$^2$, —C(=O)NR$^5$R$^6$, or

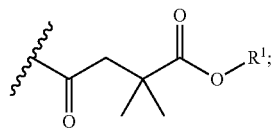

each $R^1$ is independently hydrogen, $C_1$-$C_4$ alkyl, $C_3$-$C_6$ cycloalkyl, or phenyl;

$R^2$ is $C_1$-$C_4$ alkyl, $C_3$-$C_6$ cycloalkyl, or phenyl;
$R^4$ is hydrogen, $C_1$-$C_4$ alkyl, $C_3$-$C_6$ cycloalkyl, or phenyl; and
$R^5$ and $R^6$ are each independently hydrogen, $C_1$-$C_4$ alkyl, $C_3$-$C_6$ cycloalkyl, or phenyl;
or $R^5$ and $R^6$ are taken together with the nitrogen atom to which they are attached to form a 4- to 6-membered heterocycloalkyl which is unsubstituted or is substituted with 1 or 2 substituents selected from the group consisting of $C_1$-$C_4$ alkyl and 4- to 6-membered heterocycloalkyl.

In some embodiments,
each $R^1$ is independently hydrogen, —$CH_3$, —$CH_2CH_3$, or —$CH(CH_3)_2$;
$R^2$ is —$CH_3$, —$CH_2CH_3$, —$CH(CH_3)_2$, or $C(CH_3)_3$;
$R^4$ is hydrogen, —$CH_3$, or phenyl; and
$R^3$ and $R^6$ are each independently hydrogen, —$CH_3$, or —$CH_2CH_3$;
or $R^5$ and $R^6$ are taken together with the nitrogen atom to which they are attached to form a 4- to 6-membered heterocycloalkyl which is unsubstituted or is substituted with 1 or 2 substituents selected from the group consisting of $C_1$-$C_4$ alkyl and 4- to 6-membered heterocycloalkyl.

In some embodiments, $P_1$ is —P(=O)(OH)$_2$, —CH$_2$—O—P(=O)(OH)$_2$, —S(=O)$_2$OH, —S(=O)$_2$CH$_3$, —C(=O)OCH$_2$CH$_3$, —(CH(CH$_0$))—O—C(=O)OCH(CH$_3$)$_2$, —(CH(CH$_3$))—O—C(=O)OCH$_2$CH$_3$, —C(=O)—O—(CH(phenyl))-O—C(=O)C(CH$_3$)$_3$, —C(=O)C(CH$_3$)$_3$, —CH$_2$—O—C(=O)C(CH$_3$)$_3$, —C(=O)N(CH$_3$)$_2$, or

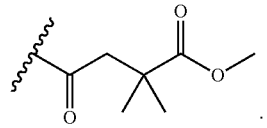 [SMILES: *C(=O)CC(C)(C)C(=O)OC]

Any combination of the groups described above for the various variables is contemplated herein. Throughout the specification, groups and substituents thereof are chosen by one skilled in the field to provide stable moieties and compounds.

Exemplary compounds of Formula (I) include the compounds described in Table 1:

TABLE 1

| Compound No. | Structure | Name |
|---|---|---|
| 1 | ![structure] | (S)-4-(3-(3-cyanoazetidin-1-yl)-2-(4-((4-(morpholinomethyl)phenyl)ethynyl)phenyl)propyl)-6-oxo-1,6-dihydropyrimidin-5-yl dihydrogen phosphate |

TABLE 1-continued

| Compound No. | Structure | Name |
|---|---|---|
| 2 | 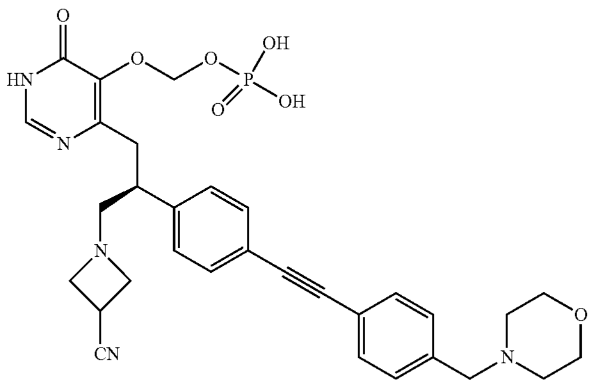 [SMILES: N#CC1CN(C[C@@H](Cc2nc[nH]c(=O)c2OCOP(=O)(O)O)c2ccc(C#Cc3ccc(CN4CCOCC4)cc3)cc2)C1] | (S)-((4-(3-(3-cyanoazetidin-1-yl)-2-(4-((4-(morpholinomethyl)phenyl)ethynyl)phenyl)propyl)-6-oxo-1,6-dihydropyrimidin-5-yl)oxy)methyl dihydrogen phosphate |
| 3 | 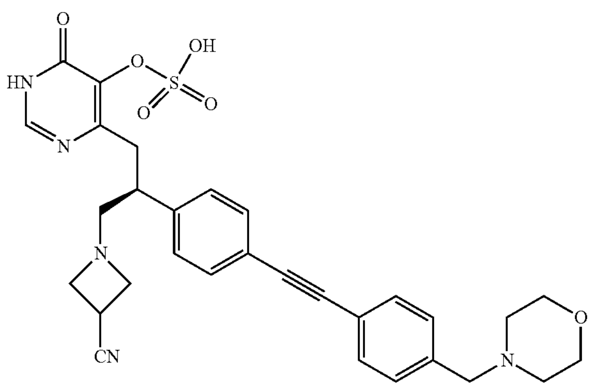 [SMILES: N#CC1CN(C[C@@H](Cc2nc[nH]c(=O)c2OS(=O)(=O)O)c2ccc(C#Cc3ccc(CN4CCOCC4)cc3)cc2)C1] | (S)-4-(3-(3-cyanoazetidin-1-yl)-2-(4-((4-(morpholinomethyl)phenyl)ethynyl)phenyl)propyl)-6-oxo-1,6-dihydropyrimidin-5-yl hydrogen sulfate |
| 4 | 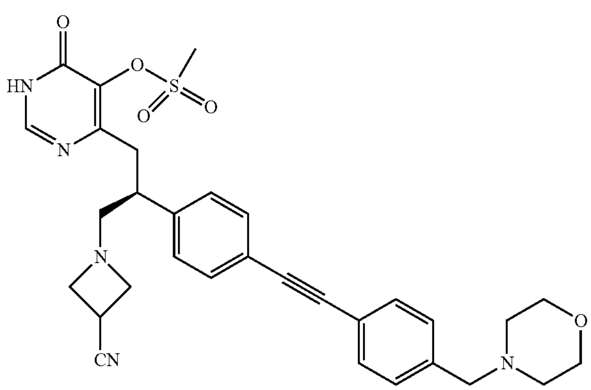 [SMILES: CS(=O)(=O)Oc1c(C[C@H](CN2CC(C#N)C2)c2ccc(C#Cc3ccc(CN4CCOCC4)cc3)cc2)nc[nH]c1=O] | (S)-4-(3-(3-cyanoazetidin-1-yl)-2-(4-((4-(morpholinomethyl)phenyl)ethynyl)phenyl)propyl)-6-oxo-1,6-dihydropyrimidin-5-yl methanesulfonate |
| 5 | 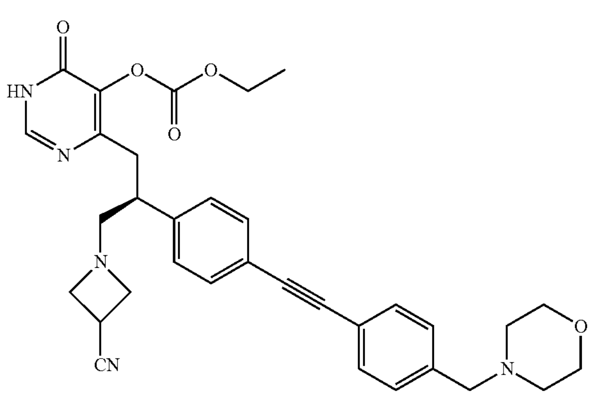 [SMILES: CCOC(=O)Oc1c(C[C@H](CN2CC(C#N)C2)c2ccc(C#Cc3ccc(CN4CCOCC4)cc3)cc2)nc[nH]c1=O] | (S)-4-(3-(3-cyanoazetidin-1-yl)-2-(4-((4-(morpholinomethyl)phenyl)ethynyl)phenyl)propyl)-6-oxo-1,6-dihydropyrimidin-5-yl ethyl carbonate |

TABLE 1-continued

| Compound No. | Structure | Name |
|---|---|---|
| 6 | 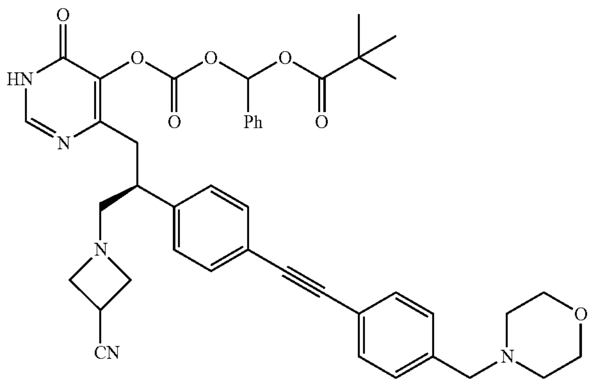 [SMILES: CC(C)(C)C(=O)OC(OC(=O)Oc1c(C[C@H](CN2CC(C#N)C2)c2ccc(C#Cc3ccc(CN4CCOCC4)cc3)cc2)nc[nH]c1=O)c1ccccc1] | ((((4-((S)-3-(3-cyanoazetidin-1-yl)-2-(4-((4-(morpholinomethyl)phenyl)ethynyl)phenyl)propyl)-6-oxo-1,6-dihydropyrimidin-5-yl)oxy)carbonyl)oxy)(phenyl)methyl pivalate |
| 7 | 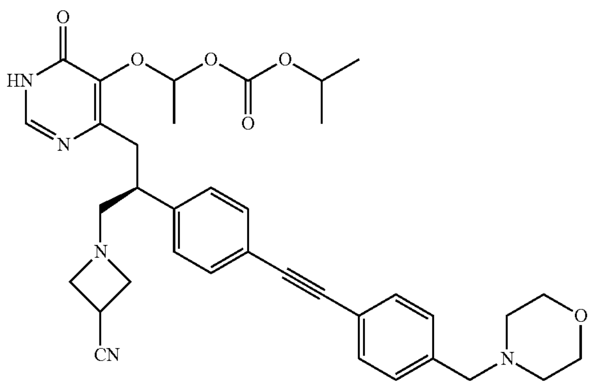 [SMILES: CC(C)OC(=O)OC(C)Oc1c(C[C@H](CN2CC(C#N)C2)c2ccc(C#Cc3ccc(CN4CCOCC4)cc3)cc2)nc[nH]c1=O] | 1-((4-((S)-3-(3-cyanoazetidin-1-yl)-2-(4-((4-(morpholinomethyl)phenyl)ethynyl)phenyl)propyl)-6-oxo-1,6-dihydropyrimidin-5-yl)oxy)ethyl isopropyl carbonate |
| 8 | 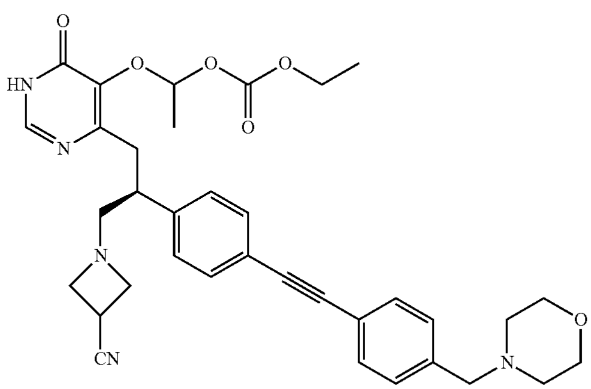 [SMILES: CCOC(=O)OC(C)Oc1c(C[C@H](CN2CC(C#N)C2)c2ccc(C#Cc3ccc(CN4CCOCC4)cc3)cc2)nc[nH]c1=O] | 1-((4-((S)-3-(3-cyanoazetidin-1-yl)-2-(4-((4-(morpholinomethyl)phenyl)ethynyl)phenyl)propyl)-6-oxo-1,6-dihydropyrimidin-5-yl)oxy)ethyl ethyl carbonate |
| 9 | 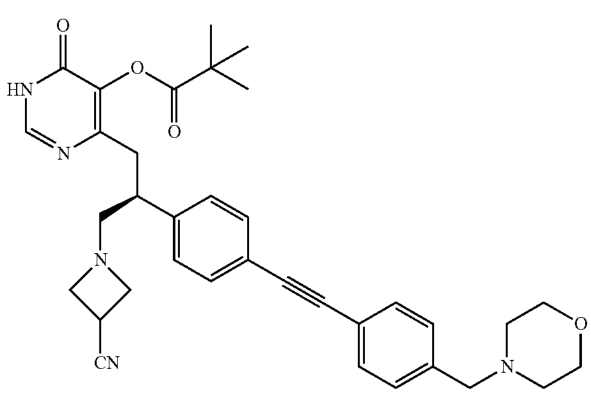 [SMILES: CC(C)(C)C(=O)Oc1c(C[C@H](CN2CC(C#N)C2)c2ccc(C#Cc3ccc(CN4CCOCC4)cc3)cc2)nc[nH]c1=O] | (S)-4-(3-(3-cyanoazetidin-1-yl)-2-(4-((4-(morpholinomethyl)phenyl)ethynyl)phenyl)propyl)-6-oxo-1,6-dihydropyrimidin-5-yl pivalate |

TABLE 1-continued

| Compound No. | Structure | Name |
|---|---|---|
| 10 | 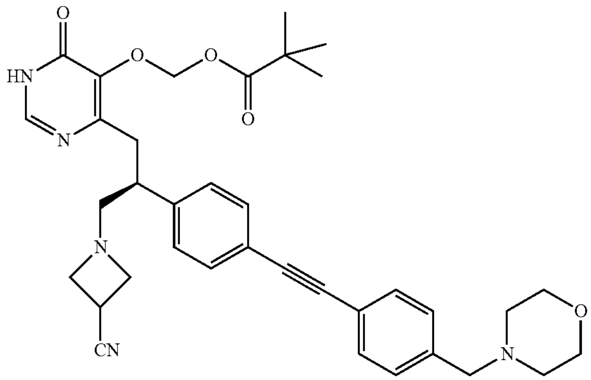 [SMILES: CC(C)(C)C(=O)OCOc1c(C[C@H](CN2CC(C#N)C2)c2ccc(C#Cc3ccc(CN4CCOCC4)cc3)cc2)nc[nH]c1=O] | (S)-((4-(3-(3-cyanoazetidin-1-yl)-2-(4-((4-(morpholinomethyl)phenyl)ethynyl)phenyl)propyl)-6-oxo-1,6-dihydropyrimidin-5-yl)oxy)methyl pivalate |
| 11 | 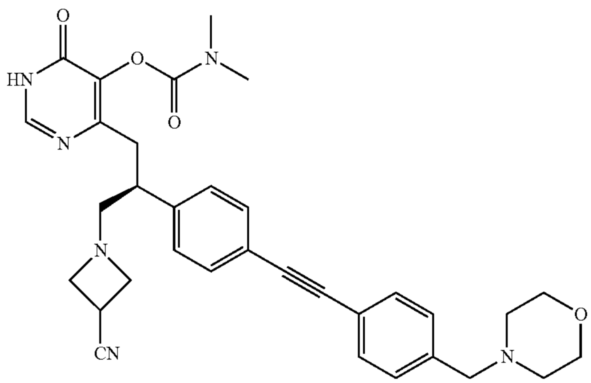 [SMILES: CN(C)C(=O)Oc1c(C[C@H](CN2CC(C#N)C2)c2ccc(C#Cc3ccc(CN4CCOCC4)cc3)cc2)nc[nH]c1=O] | (S)-4-(3-(3-cyanoazetidin-1-yl)-2-(4-((4-(morpholinomethyl)phenyl)ethynyl)phenyl)propyl)-6-oxo-1,6-dihydropyrimidin-5-yl dimethylcarbamate |
| 12 | 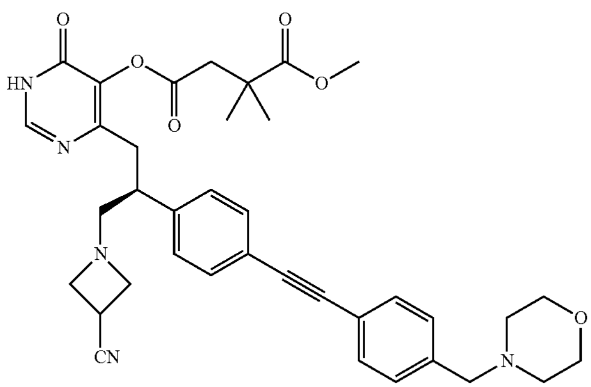 [SMILES: COC(=O)C(C)(C)CC(=O)Oc1c(C[C@H](CN2CC(C#N)C2)c2ccc(C#Cc3ccc(CN4CCOCC4)cc3)cc2)nc[nH]c1=O] | (S)-4-(4-(3-(3-cyanoazetidin-1-yl)-2-(4-((4-(morpholinomethyl)phenyl)ethynyl)phenyl)propyl)-6-oxo-1,6-dihydropyrimidin-5-yl) 1-methyl 2,2-dimethylsuccinate |

In some embodiments, the compound is a pharmaceutically acceptable salt of a compound in Table 1. In some embodiments, the compound is a pharmaceutically acceptable solvate of a compound of Table 1.

Definitions

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like.

"Cycloalkyl" refers to a stable monocyclic or polycyclic hydrocarbon radical consisting solely of carbon and hydrogen atoms, which includes fused or bridged ring systems, containing no unsaturation, having from three to fifteen carbon atoms. In certain embodiments, a cycloalkyl comprises three to ten carbon atoms. In other embodiments, a cycloalkyl comprises three to six carbon atoms. Examples of monocyclic cycloalkyls include, e.g., cyclopropyl, cyclobutyl, cyclopentyl, cyclohexyl, cycloheptyl, and cyclooctyl. The cycloalkyl is attached to the rest of the molecule by a single bond.

"Heterocycloalkyl" refers to a stable 3- to 18-membered ring radical that comprises two to twelve carbon atoms and from one to six heteroatoms selected from nitrogen, oxygen and sulfur, containing no unsaturation. Unless stated otherwise specifically in the specification, the heterocycloalkyl radical is a monocyclic, bicyclic, tricyclic or tetracyclic ring system, which optionally includes fused, bridged, or spirocyclic ring systems. The heteroatoms in the heterocycloalkyl radical are optionally oxidized. One or more nitrogen atoms, if present, are optionally quaternized. In certain embodiments the heterocycloalkyl comprises three to ten atoms in the ring. In other embodiments, the heterocycloalkyl comprises from four to six atoms in the ring. Examples of monocyclic heterocycloalkyl radicals include, but are not limited to, aziridine, oxirane, thiirane, azetidine, oxetane, thietane, pyrrolidine, tetrahydrofuran, tetrahydrothiophene, imidazolidine, pyrazolidine, oxazolidine, isoxazolidine, thiazolidine, isothiazolidine, piperidine, tetrahydropyran, morpholine, thiomorpholine, dioxane, dithiane, azepane, oxepane, and homomorpholine. The heterocycloalkyl is attached to the rest of the molecule through any atom of the ring(s), for example a carbon atom (C-linked heterocycloalkyl) or a nitrogen atom (N-linked heterocycloalkyl).

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. In certain embodiments, the heteroaryl is a monocyclic heteroaryl. In some embodiments, the heteroaryl is a 5-membered heteroaryl. In other embodiments, the heteroaryl is a 6-membered heteroaryl. Examples of monocyclic heteroaryls include, but are not limited to, pyrrole, furan, thiophene, imidazole, pyrazole, oxathiole, isoxathiole, oxazole, isoxazole, thiazole, isothiazole, triazole, oxadiazole, thiadiazole, tetrazole, pyridine, pyridazine, pyrimidine, pyrazine, and triazine. The heteroaryl is attached to the rest of the molecule through any atom of the ring.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally. In some embodiments, the compounds and compositions described herein are administered intravenously.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. the LpxC inhibitory compound disclosed herein, or an isotopic variant, tautomer, prodrug, pharmaceutically acceptable salt, solvate, or hydrate thereof, and a co-agent, are both administered to a patient simultaneously in the form of a single entity or dosage. The term "non-fixed combination" means that the active ingredients, e.g. the LpxC inhibitory compound disclosed herein, or an isotopic variant, tautomer, prodrug, pharmaceutically acceptable salt, solvate, or hydrate thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats, laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Further Forms of Compounds

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound disclosed herein with an acid. In some embodiments, the compound disclosed herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid, acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoicacid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D), glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1, 5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, pharmaceutically acceptable salts are obtained by reacting a compound disclosed herein with a base. In some embodiments, the compound disclosed herein is acidic and is reacted with a base. In such situations, an acidic proton of the compound disclosed herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

A "tautomer" refers to a molecule wherein a proton shift from one atom of a molecule to another atom of the same molecule is possible. In some instances, the heterocyclic LpxC inhibitory compounds disclosed herein exist in tautomeric forms. The structures of said compounds are illustrated in the one tautomeric form for clarity. The alternative tautomeric forms are expressly included in this disclosure, such as, for example, the structures illustrated below.

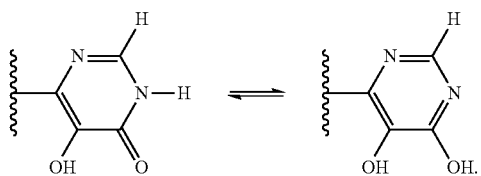 [SMILES: *c1nc[nH]c(=O)c1O ; *c1ncnc(O)c1O]

In some embodiments, sites on the organic radicals (e.g. alkyl groups, aromatic rings) of compounds disclosed herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or altered metabolic pathways to reduce undesirable metabolites or reduced dosage requirements.

In some embodiments, one or more hydrogen atoms on the compound disclosed herein are replaced with deuterium. In some embodiments, substitution with deuterium affords certain therapeutic advantages resulting from greater metabolic stability, such as, for example, increased in vivo half-life or reduced dosage requirements.

In one aspect, described is a compound with the following structure:

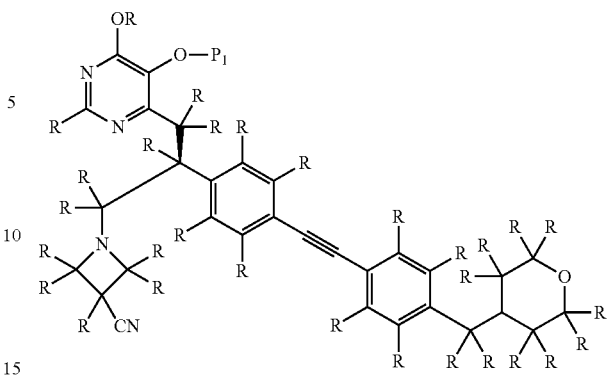

wherein,
each R is independently selected from hydrogen or deuterium, and
$P_1$ is as described herein, where each hydrogen atom can be optionally replaced with a deuterium atom,
or an isotopic variant, tautomer, pharmaceutically acceptable salt, solvate, or hydrate thereof.

In some embodiments, the compounds disclosed herein possess one or more stereocenters and each stereocenter exists independently in either the R or S configuration. For example, in some embodiments, the compound disclosed herein exists in the R configuration when one stereocenter is present. In other embodiments, the compound disclosed herein exists in the S configuration when one stereocenter is present. In some embodiments, the compound disclosed herein exists in the RR configuration when two stereocenters are present. In some embodiments, the compound disclosed herein exists in the RS configuration when two stereocenters are present. In some embodiments, the compound disclosed herein exists in the SS configuration when two stereocenters are present. In some embodiments, the compound disclosed herein exists in the SR configuration when two stereocenters are present.

The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds disclosed herein are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers of compounds disclosed herein is carried out using covalent diastereomeric derivatives of the compounds described herein. In another embodiment, diastereomers of compounds disclosed herein are separated by separation/resolution techniques based upon differences in solubility. In other embodiments, separation of stereoisomers of compounds disclosed herein is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

Separation of individual enantiomers from a racemic mixture is possible by the use of chiral supercritical fluid chromatography (SFC) or chiral high performance liquid chromatography (HPLC). In some embodiments, enantiomers described herein are separated from each other by the use of chiral SFC or chiral HPLC. In some embodiments, compounds disclosed herein that include one or more chiral centers (e.g. compounds disclosed herein that include the moiety trans-octahydro-1H-pyrido[3,4-b]morpholin-6-yl) are separated into individual enantiomers using chiral SFC or chiral HPLC. A wide variety of conditions and suitable columns are available.

Daicel polysaccharide chiral stationary phases (CSPs) are among the columns used for chiral SFC separations. In some embodiments, Daicel analytical immobilised and coated CHIRALPAK and CHIRALCEL HPLC columns can be used for SFC analysis.

In some embodiments, screening for the suitability of using a SFC column is performed on the four main immobilised phases (CHIRALPAK IA, IB, IC and ID) and the four main coated columns (CHIRALPAK AD and AS and CHIRALCEL OD and OJ), with varying concentrations of organic modifier. A variety of column phases are available, including but not limited to OD and GJ, OX and OZ chlorinated phases, and a range of complementary cellulose based CHIRALCEL phases including OA, OB, OC, OF, OG and OK.

Non-limiting examples of chiral selectors contemplated for use in the separation of enantiomers include amylose tris (3, 5-dimethylphenylcarbamate), cellulose tris (3, 5-dimethylphenylcarbamate), cellulose tris (3, 5-dichlorophenylcarbamate), amylose tris (3-chlorophenylcarbamate), amylosetris (3, 5-dichlorophenylcarbamate), amylosetris (3-chloro, 4-methylphenylcarbamate), amylose tris ((S)-alpha-methylbenzylcarbamate), amylose tris (5-chloro-2-methylphenylcarbamate), cellulose tris (4-methylbenzoate), cellulose tris (4-chloro-3-methylphenylcarbamate), and cellulose tris (3-chloro-4-methylphenylcarbamate).

Non-limiting examples of chiral columns contemplated for use in the separation of enantiomers include CHIRALPAK IA SFC, CHIRALPAK AD-H SFC, CHIRALPAK IB SFC, CHIRALCEL OD-H SFC, CHIRALPAK IC SFC, CHIRALPAK ID SFC, CHIRALPAK IE SFC, CHIRALPAK IF SFC, CHIRALPAK AZ-H SFC, CHIRALPAK AS-H SFC, CHIRALPAK AY-H SFC, CHIRALCEL OJ-H SFC, CHIRALCEL OX-H SFC, and CHIRALCEL OZ-H SFC.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Pharmaceutical Compositions

In certain embodiments, the LpxC inhibitory compound as described herein is administered as a pure chemical. In other embodiments, the LpxC inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)).

Provided herein is a pharmaceutical composition comprising at least one LpxC inhibitory compound as described herein, or a stereoisomer, pharmaceutically acceptable salt, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

One embodiment provides a pharmaceutical composition comprising the LpxC inhibitory compound as described herein, or a pharmaceutically acceptable salt, or solvate thereof, and at least one pharmaceutically acceptable excipient.

In some embodiments, the pharmaceutical composition is in a dosage form for dosing or administration by injection. In some embodiments, the pharmaceutical composition is in a dosage form for intravenous (I.V.) injection or infusion, or intramuscular, subcutaneous, or intradermal injection. In some embodiments, the pharmaceutical composition is in a dosage form for I.V injection or infusion. In some embodiments, the pharmaceutical composition is a solution.

In some embodiments, the pharmaceutical composition is in a dosage form for oral dosing or administration. In some embodiments, the dosage form is a liquid. In some embodiments, the dosage form is a suspension, solution, syrup, or elixir. In some embodiments, the dosage form is a suspension. In some embodiments, the dosage form is a nanosuspension. In some embodiments, the dosage form is a solution. In other embodiments, the dosage form is a tablet or a capsule.

In some embodiments, the at least one pharmaceutically acceptable excipient is a co-solvent, oil, surfactant, complexing agent, a solubilizing polymer, a P-gp modulator, a buffering agent, or a combination thereof.

In certain embodiments, the heterocyclic LpxC inhibitory compound disclosed herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Pharmaceutical compositions are administered in a manner appropriate to the disease to be treated (or prevented).

An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

LpxC, Lipid a and Gram-Negative Bacteria

Metalloproteins influence a vast diversity of biological systems, biological processes, and diseases. For example, UDP-{3-O—[(R)-3-hydroxymyristoyl]}-N-acetylglucosamine deacetylase (LpxC) is an essential enzyme involved in the first committed step in lipid A biosynthesis for gram-negative bacteria. Lipid A is an essential component of the outer membrane of gram-negative bacteria. LpxC is a zinc(II)-dependent metalloenzyme, with two histidines and an aspartic acid residue bound to the zinc(II) ion. Structures of LpxC show the zinc(II) ion is bound to two water molecules, both of which have been implicated in the mechanism of the enzyme. LpxC is highly conserved across strains of gram-negative bacteria, making LpxC an attractive target to treat gram-negative infections.

In recent years, there has been an increase in resistant and multi-drug resistant strains of bacteria. Thus, there is a need for new antibiotics, especially with new mechanisms of action. There remains a need for metalloprotein modulators of LpxC useful in the field of therapeutics, diagnostics, and research.

One embodiment provides a method of inhibiting UDP-{3-O—[(R)-3-hydroxymyristoyl]}-N-acetylglucosamine deacetylase enzyme comprising contacting the enzyme with the LpxC inhibitory compounds disclosed herein.

Methods of Treatment

Disclosed herein are methods of treating disease wherein the inhibition of bacterial growth is indicated. Such disease includes gram-negative bacterial infection. In some embodiments, the method of treating a gram-negative bacterial infection in a patient in need thereof comprises administering to the patient a pharmaceutical composition comprising an LpxC inhibitory compound disclosed herein, or an isotopic variant, tautomer, prodrug, pharmaceutically acceptable salt, solvate, or hydrate thereof, and a pharmaceutically acceptable excipient. In some embodiments, the gram-negative bacterial infection is selected from pneumonia, sepsis, cystic fibrosis, intra-abdominal infection, skin infections and urinary tract infection. In some embodiments, the gram-negative bacterial infection is a urinary tract infection (UTI), a hospital acquired/ventilator-associated pneumonia (HAP/VAP), or an intra-abdominal infection (IAI). In some embodiments, the gram-negative bacterial infection is selected from chronic urinary tract infections, complicated urinary tract infections, cystitis, pyelonephritis, urethritis, recurrent urinary tract infections, bladder infections, urethral infections, and kidney infections. In some embodiments, the compounds described herein are used for the treatment of chronic urinary tract infections. In some embodiments, the compounds described herein are used for the treatment of complicated urinary tract infections. In other embodiments, the compounds described herein are used for the treatment of complicated intra-abdominal infection. In some embodiments, the compounds described herein are used for the treatment of chronic intra-abdominal infection. In other embodiments, the compounds described herein are used for the treatment of hospital acquired pneumonia (HAP) or ventilator associated pneumonia (VAP). In some embodiments the administration is to treat an existing infection. In some embodiments the administration is provided as prophylaxis.

In some embodiments, the LpxC inhibitory compounds described herein, or an isotopic variant, tautomer, prodrug, pharmaceutically acceptable salt, solvate, or hydrate thereof, ae used for treating conditions caused by the bacterial production of endotoxin and, in particular, by gram-negative bacteria and bacteria that use LpxC in the biosynthesis of lipopolysaccharide (LPS) or endotoxin. In some embodiments, the method of treating a condition caused by endotoxin or LPS in a patient in need thereof comprises administering to the patient a pharmaceutical composition comprising an LpxC inhibitory compound disclosed herein, or an isotopic variant, tautomer, prodrug, pharmaceutically acceptable salt, solvate, or hydrate thereof, and a pharmaceutically acceptable excipient. In another embodiment, the heterocyclic LpxC inhibitory compounds and formulations as described herein are useful in the treatment of conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). In some embodiments, the method of treating a condition caused by endotoxin or LPS in a patient in need thereof comprises administering to the patient a pharmaceutical composition comprising the LpxC inhibitory compounds disclosed herein, or an isotopic variant, tautomer, prodrug, pharmaceutically acceptable salt, solvate, or hydrate thereof, and a pharmaceutically acceptable excipient, wherein the condition caused by endotoxin or LPS is selected from sepsis, septic shock, systemic inflammation, localized inflammation, chronic obstructive pulmonary disease (COPD) and acute exacerbations of chronic bronchitis (AECB).

In other embodiments, the LpxC inhibitory compounds described herein, or an isotopic variant, tautomer, prodrug, pharmaceutically acceptable salt, solvate, or hydrate thereof, can be used for the treatment of a serious or chronic respiratory tract infection or complicated urinary tract infections including serious lung and nosocomial infections such as those caused by *Enterobacter aerogenes, Enterobacter cloacae, Escherichia coli, Klebsiella pneumoniae, Klebsiella oxytoca, Kluyvera ascorbata, Kluyvera cryocrescense, Shigella sonnei, Proteus mirabilis, Serratia marcescens, Stenotrophomonas maltophilia, Pseudomonas aeruginosa, Burkholderia cepacia, Acinetobacter baumannii, Alcaligenes xylosoxidans, Flavobacteriurm meningosepticum, Providencia shuarlii* and *Citrobacter freundii, Haemophilus influenzae, Kluyvera species, Legionella species, Moraxella catarrhalis, Enterobacter species, Acinetobacter species, Klebsiella species, Burkholderia species* and *Proteus species*, and infections caused by other bacterial species such as *Neisseria species, Shigella species, Salmonella species, Helicobacler pylori, Vibrionaceae* and *Bordetella species* as well as the infections caused by a *Brucella species, Francisella tularensis* and/or *Yersinia pestis*.

In one embodiment provided herein is a method of treating a gram-negative bacterial infection in a patient in need thereof comprising administering to the patient a pharmaceutical composition comprising an LpxC inhibitory compound disclosed herein, or an isotopic variant, tautomer, prodrug, pharmaceutically acceptable salt, solvate, or hydrate thereof, and at least one pharmaceutically acceptable excipient.

One embodiment provides a method wherein the gram-negative bacterial infection is selected from pneumonia, sepsis, cystic fibrosis, intra-abdominal infection, skin infection and urinary tract infection.

One embodiment provides a method wherein the gram-negative bacterial infection is selected from chronic urinary tract infection, complicated urinary tract infection, cystitis, pyelonephritis, urethritis, recurrent urinary tract infections, bladder infections, urethral infections and kidney infections.

One embodiment provides a method wherein the gram-negative bacterial infection is chronic urinary tract infections. One embodiment provides a method wherein the gram-negative bacterial infection is complicated urinary tract infections. One embodiment provides a method wherein the administration is to treat an existing infection. One embodiment provides a method wherein the administration is provided as prophylaxis.

In some embodiments, the LpxC inhibitory compounds described herein, or isotopic variants, tautomers, prodrugs, pharmaceutically acceptable salts, solvates, or hydrates thereof, are not active against gram-positive bacteria. In some embodiments, the LpxC inhibitory compounds described herein, or isotopic variants, tautomers, prodrugs, pharmaceutically acceptable salts, solvates, or hydrates thereof, are not active against *Staphylococcus aureus, Enterococcus faecalis, Streptococcus pyogenes, Bacillus thuringiensis, Lactobacillus rhamnosus, Staphylococcus epidermidis, Bifidobacterium breve, Clostridium difficile, Clostridium sordellii, Peptostreptococcus anaerobius, Streptococcus pneumoniae, Corynebacterium jeikeium, Propionibacterium acnes, Listeria monocytogenes,* and/or *Nocardia cyriacigeorgica* complex. Most gut bacteria are Gram-positive, including *C. difficile*. Therefore, in some embodiments, the lack of activity against gram-positive bacteria is a benefit. In some embodiments, use of the LpxC inhibitory compounds described herein, or isotopic variants, tautomers, prodrugs, pharmaceutically acceptable salts, solvates, or hydrates thereof, to treat a gram-negative bacterial infection, as described herein, has no effect on the gut microflora and thus reduces the risk of secondary infections from, for example, *C. difficile*.

Combination Therapy

In some instances, Gram-negative bacteria are more resistant to a larger number of antibacterials and chemotherapeutic agents than are gram-positive bacteria due in part to their outer membrane, which acts as an efficient permeability barrier.

A survey of recently reported antibacterials of natural origin showed that over 90% lacked activity against *Escherichia coli*, although they were active against gram-positive bacteria. Young and Silver (J. Bacteriol. 173(12):3609-14 (1991)) demonstrated that an envA1 strain, having an altered outer membrane, is sensitive to a variety of large and hydrophobic antibacterials to which wild type *E. coli* is resistant. Additionally, Vaara, et al., (Antimicrobial Agents and Chemotherapy 37(11):2255-2260 (1993)) review a variety of outer membrane-defective mutants of E cob and *S. typhimurium* that show greater susceptibility than the corresponding wild type strain to a variety of antibacterial agents.

In some embodiments, the present invention provides synergistic combinations of antibacterial agents with the LpxC inhibitory compounds or pharmaceutical compositions disclosed herein. In some embodiments, the LpxC inhibitory compounds disclosed herein have both intrinsic antibacterial properties as well the ability to improve permeability of the outer membrane of gram-negative bacteria to other antibacterial agents. In some embodiments, the antibacterial agent is selected from the group consisting of vancomycin, linezolid, azithromycin, imipenem, teicoplanin, daptomycin, clindamycin, rifampin, cefotaxime, gentamicin, novobiocin, and telavancin.

The use of such synergistic combinations of drugs could have many advantages over conventional single compound therapy, including lowered side-effects of the antibacterial agent due to lower doses used or to shorter time of treatment, more rapid cure of infection shortening hospital stays, increasing spectrum of pathogens controlled, and decreasing incidence of development of resistance to antibiotics.

Methods of Dosing and Treatment Regimens

In one embodiment, the LpxC inhibitory compounds disclosed herein, or an isotopic variant, tautomer, prodrug, pharmaceutically acceptable salt, solvate, or hydrate thereof, are used in the preparation of medicaments for the treatment of diseases or conditions in a mammal that would benefit from modulation of LpxC activity. Methods for treating any of the diseases or conditions described herein in a mammal in need of such treatment, involves administration of pharmaceutical compositions that include the LpxC inhibitory compounds disclosed herein, or an isotopic variant, tautomer, prodrug, pharmaceutically acceptable salt, solvate, or hydrate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the LpxC inhibitory compounds disclosed herein, or an isotopic variant, tautomer, prodrug, pharmaceutically acceptable salt, solvate, or hydrate thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

In any of the aforementioned aspects are further embodiments in which the effective amount of the LpxC inhibitory compounds disclosed herein, or an isotopic variant, tautomer, prodrug, pharmaceutically acceptable salt, solvate, or hydrate thereof, is: (a) systemically administered to the mammal; and/or (b) administered orally to the mammal.

In some embodiments, the LpxC inhibitory compound disclosed herein, or an isotopic variant, tautomer, prodrug, pharmaceutically acceptable salt, solvate, or hydrate thereof, is administered is dose selected from about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, and about 400 mg. In some embodiments, the dose is administered once a day. In some embodiments, the dose is administered twice a day.

Articles of Manufacture and Kits

Disclosed herein, in certain embodiments, are kits and articles of manufacture for use with one or more methods described herein. In some embodiments, additional components of the kit comprises a carrier, package, or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use.

For example, the container(s) include one or more of the compounds described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

The following abbreviations and terms have the indicated meanings throughout:

ACN=acetonitrile
DCM=dichloromethane
DMF=N,N-Dimethylformamide
EtOAc=ethyl acetate
g=gram
h or hr=hour
HPLC=high pressure liquid chromatography
LCMS=liquid chromatography-mass spectrometry
m/z=mass-to-charge ratio
mg=milligram
min=minute
mL=milliliter
mmol=millimole
PBS=phosphate-buffered saline
RP-HPLC=reverse phase-high pressure liquid chromatography
rt or RT=room temperature
TFA=trifluoroacetic acid The following examples are provided for illustrative purposes only and not to limit the scope of the claims provided herein.

Example 1: Preparation of (S)-1-(3-(5,6-dihydroxypyrimidin-4-yl)-2-(4-((4-(morpholinomethyl)phenyl)ethynyl)phenyl)propyl)azetidine-3-carbonitrile (Compound A)

The preparation and use of Compound A has been previously described (see, WO 2020/061375, US 2021/0221796, WO 2021/195260, and US 2021/0309651 each of which is incorporated by reference in its entirety).

Example 2: Preparation of (S)-(4-(3-(3-cyanoazetidin-1-yl)-2-(4-((4-(morpholinomethyl)phenyl)ethynyl)phenyl)propyl)-6-oxo-1,6-dihydropyrimidin-5-yl)oxy)methyl dihydrogen phosphate (Compound 2)

filtered through Buchner funnel. The filtrate was further purified by column chromatography (SiO$_2$ 100-200 mesh; EtOAc and DCM) to afford 2-2 (200 mg, 45%) as gum. LCMS: Calculated for $C_{48}H_{69}N_5O_{11}P_2$: 954.05 (Exact mass: 953.45); Observed: 953.9 [M+1]$^+$.

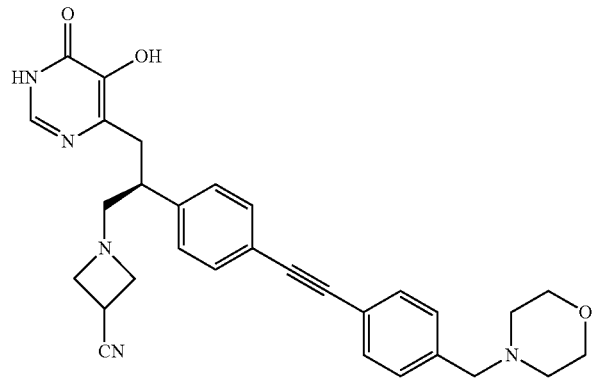

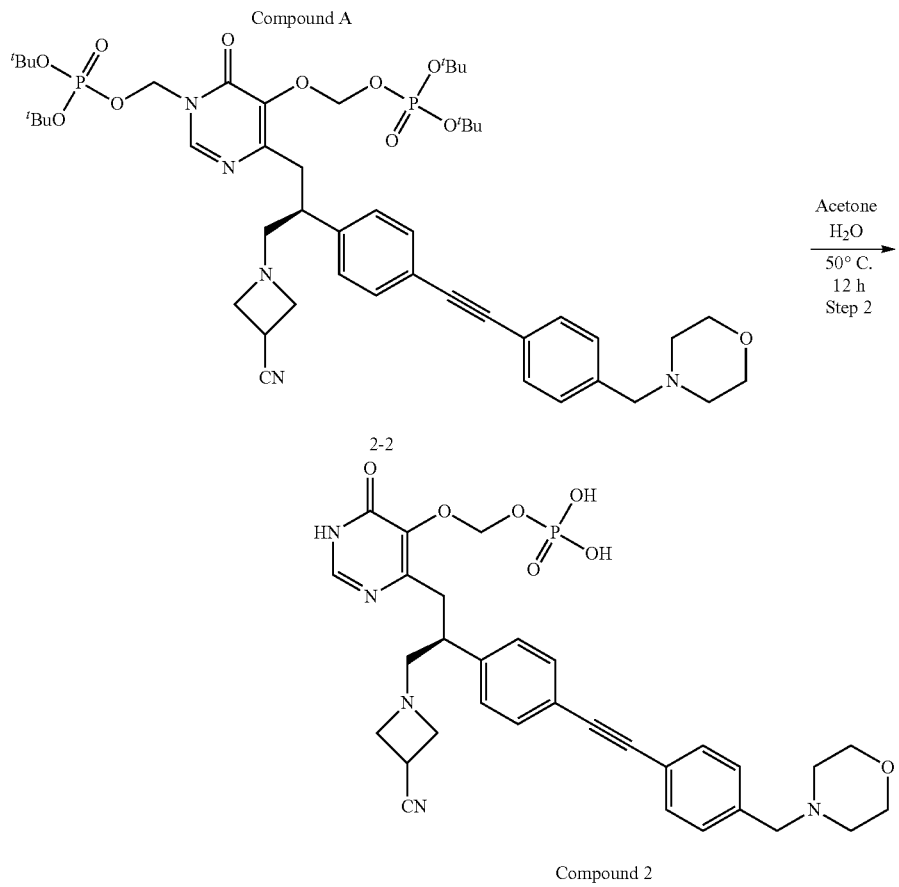

Step 1: To a stirred suspension of Compound A (0.2 g, 0.392 mmol) in DMF (10 mL), were added potassium carbonate (0.054 g, 0.392 mmol) and di-tert-butyl(chloromethyl)phosphate (2-1, 0.508 g, 1.962 mmol) at 25° C. After stirring for 12 h, LCMS showed complete consumption of starting material and the formation of mono and dialkylated products. The reaction mixture was filtered, and the filtrate was concentrated under reduced pressure. The crude product was triturated with diethyl ether. The solid precipitated was Step 2: A solution of 2-2 (0.1 g, 0.105 mmol) in acetone (5 mL) and water (5 mL) was heated at 50° C. for 12 h. The progress of the reaction was monitored by LCMS. The volatiles were evaporated under reduced pressure and the crude product was purified by reversed phase prep HPLC (0.10% TFA in water buffer and acetonitrile) to afford Compound 2 (12.26 mg, 19%) as an off-white solid. LCMS: Calculated for $C_{31}H_{34}N_5O_7P$: 619.61; Observed: 620.0 [M+1]$^+$.

Example 3: Preparation of (S)₄-(3-(3-cyanoazetidin-1-yl)-2-(4-((4-(morpholinomethyl)phenyl)ethynyl)phenyl)propyl)-6-oxo-1,6-dihydropyrimidin-5-yl dihydrogen phosphate (Compound 1)

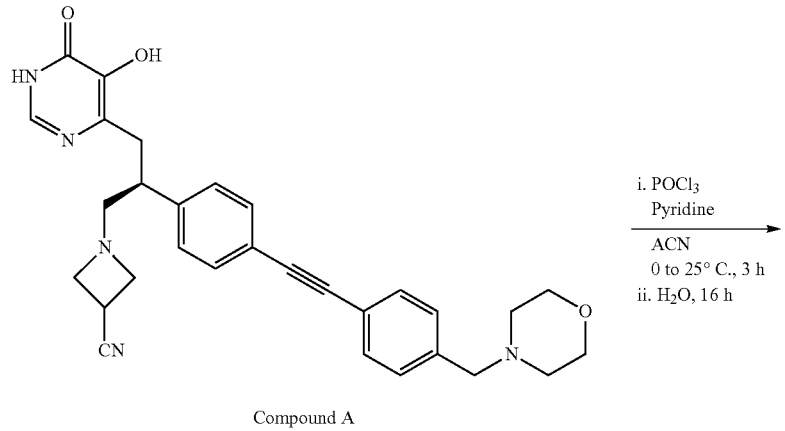

Compound A i. POCl₃
   Pyridine
   ───────
   ACN
   0 to 25° C., 3 h
ii. H₂O, 16 h

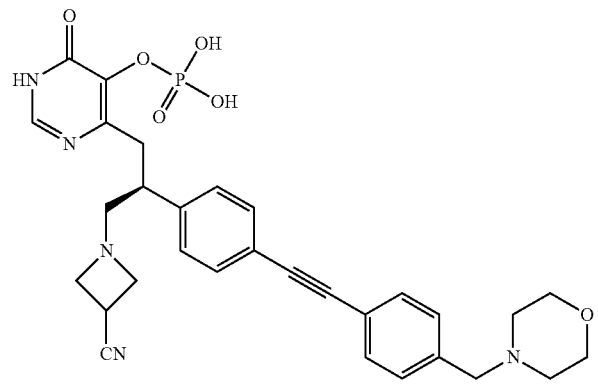

Compound 1

To a solution of Compound A (0.2 g, 0.392 mmol) in pyridine (8 mL), was added phosphoryl trichloride (0.093 mL, 0.995 mmol) at 0° C. The reaction mixture was stirred at 25° C. for 1 h. To this reaction mixture was added acetonitrile (9.6 mL) and stirred at 25° C. for 2 h. The reaction was quenched with water (10 mL) and stirred for 16 h at 25° C. The reaction mixture was concentrated. The resulting crude product was purified by reversed phase preparative HPLC (10 mM ammonium bicarbonate buffer and acetonitrile) to afford Compound 1 (45 mg, 19%) as pale pink solid. LC-MS: Calculated for $C_{30}H_{32}N_5O_6P$: 589.59, Observed: 590.7 [M+1]⁺.

Example 4: Preparation of (S)-4-(3-(3-cyanoazetidin-1-yl)-2-(4-((4-(morpholinomethyl)phenyl)ethynyl)phenyl)propyl)-6-oxo-1,6-dihydropyrimidin-5-yl dimethylcarbamate (Compound 11)

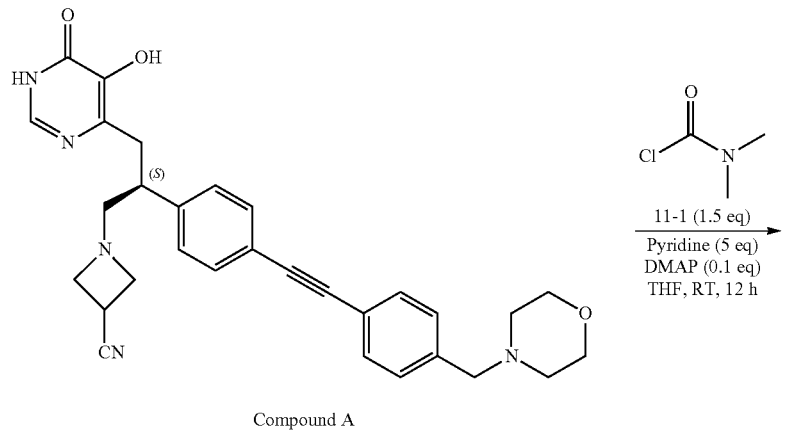

Compound A

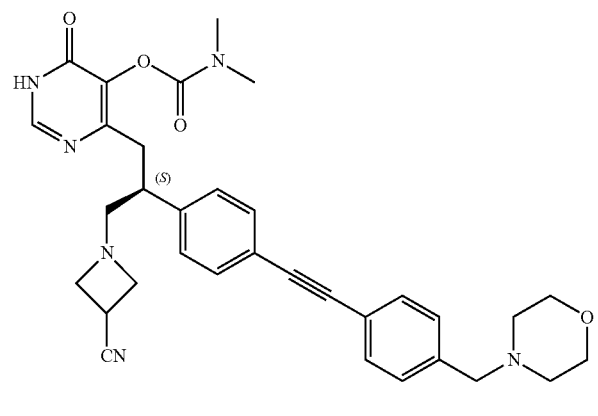

Compound 11

To a stirred suspension of Compound A (0.25 g, 0.491 mmol) in THF (25 ml), pyridine (0.198 ml, 2.453 mmol), dimethylcarbamoyl chloride, 1-1 (0079 g, 0.736 mmol) and 4-dimethylaminopyridine (5.99 mg, 0.049 mmol) were added and stirred at 25° C. for 12 h. The reaction mixture was filtered off to remove unreacted starting material, the filtrate was concentrated under reduced pressure and the crude product was purified by reverse phase prep HPLC in 0.1% TFA/acetonitrile to afford Compound 11 as an off-white solid. Yield: 30 mg, (10% yield). LC-MS: Calculated for $C_{33}H_{36}N_6O_4$: 580.68, Observed: 581.0 [M+H]$^+$; 603 (M+Na)$^+$; 291 (M+2)$^{2+}$/2.

Example 5: Preparation of (S)-4-(4-(3-(3-cyanoazetidin-1-yl)-2-(4-((4-(morpholinomethyl)phenyl)ethynyl)phenyl)propyl)-6-oxo-1,6-dihydropyrimidin-5-yl) 1-methyl 2,2-dimethylsuccinate (Compound 12)

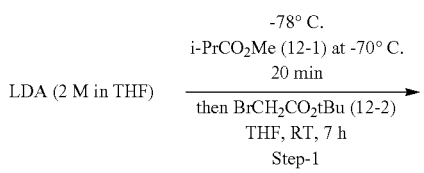

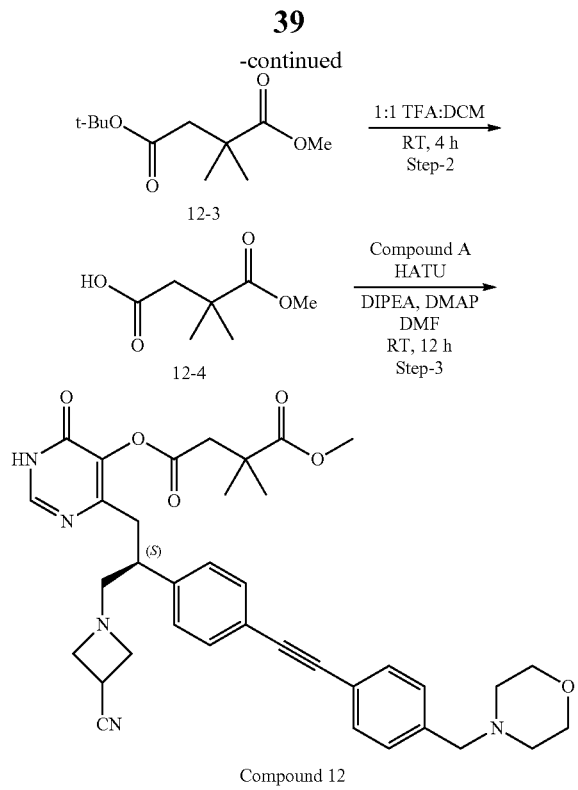

Compound 12

Step 1: A solution of lithium diisopropylamide (2 M in THF, 4.90 mL, 9.79 mmol) was diluted with Tetrahydrofuran (15 mL), and the mixture was cooled to −78° C. methyl isobutyrate (12-1, 1 g, 9.79 mmol) was added dropwise and the mixture was stirred at −70° C. to −65° C. for 20 minutes. tert-butyl 2-bromoacetate (12-2, 5.6 mL, 11.74 mmol) was added dropwise. The reaction mixture was allowed to warm to RT and stirred for 7 h. TLC showed consumption of starting material. The reaction mixture was quenched with saturated NH$_4$Cl (aq). The aqueous layer was extracted with ethyl acetate. The organic layer was separated and dried over anhydrous Na$_2$SO$_4$, filtered and concentrated under reduced pressure to afford 4-(tert-butyl) 1-methyl 2,2-dimethylsuccinate (12-3, 1 g, 4.62 mmol, 47% yield) as brown oil. The crude mass as such taken to the next step.

Step 2: A solution of 50% TFA (10.00 mL) in DCM (10 mL) was added to 4-(tert-butyl) 1-methyl 2,2-dimethylsuccinate (12-3, 1 g, 4.62 mmol) and stirred at RT for 4 h. TLC showed consumption of starting material. The reaction mixture was concentrated under reduced pressure to remove TFA and DCM. The reaction mixture was basified with 10% sodium bicarbonate solution (30 mL), washed with DCM. The aqueous layer was acidified with 0.1 N HCl and extracted with DCM. The organic layer was dried over anhydrous Na$_2$SO$_4$, filtered and concentrated under reduced pressure to obtain 4-methoxy-3,3-dimethyl-4-oxobutanoic acid (12-4, 0.7 g, 3.69 mmol, 80% yield) as brown oil. The crude mass as such taken to the next step. LC-MS: Calculated for C$_7$H$_{12}$O$_4$: 160.17; Observed: 161 [M+H]$^+$ and 143 [M−H$_2$O]$^+$.

Step 3: To a stirred solution of 4-methoxy-3,3-dimethyl-4-oxobutanoic acid (12-4, 0.100 g, 0.196 mmol), HATU (0.298 g, 0.785 mmol), N-ethyl-N-isopropylpropan-2-amine (0.101 g, 0.785 mmol) in DMF (2 mL), 4-(dimethylamino) pyridine (0.024 g, 0.196 mmol) were added and stirred. Compound A (0.1 g, 0.196 mmol) in DMF (2 mL) was added and stirred at RT for 12 h. The reaction mixture was washed with water and extracted with ethyl acetate (2×20 mL). The organic layer was dried over anhydrous Na$_2$SO$_4$, filtered and concentrated under reduced pressure. The crude compound was purified by preparatory HPLC to obtain Compound 12 (45 mg, 0.067 mmol, 34% yield) as white solid. LC-MS. Calculated for C$_{37}$H$_{41}$N$_5$O$_6$: 651.76; Observed: 652.2 [M+H]$^+$; 510 [M-acyl group]$^+$; 326.7 [M+2]$^{2+}$/2.

Example 6: Thermal Solubility

Solubility of the compounds was assessed in 100 mM potassium phosphate buffer at pH 7.4 after 24 hours at room temperature.

Accurately weighed K$_2$HPO$_4$ (2.79 g) and KH$_2$PO$_4$ (0.54 g) were dissolved in 90 mL of Milli-Q water and mixed well. Volume was made upto 200 mL with Milli-Q water and mixed well. The prepared phosphate buffer was stored at 2-8° C. and used within a month.

Approximately 30 mg of test compound was added to approximately 1 mL of the potassium phosphate buffer, pH 7.4. If the visual inspection indicated precipitation, no further compound is added. If the visual inspection indicated a clear solution, further increments of compound were added until the solution was no longer clear.

Test compounds and assay controls (caffeine) were further incubated for 24 h at 25° C. temperature on a thermomixer at a shaking speed of 1200 rpm. After incubation, the samples (200 µL) were transferred to a filtration plate to which a plate was attached at bottom for collecting the filtrate. The plate was centrifuged at 4000 rpm for 2 min and the filtrate was collected in the attached bottom plate. The filtrates were diluted using filtered buffer based on the initial amount of compound added. All samples were analysed by HPLC-UV method against 8 point calibration curve with concentrations ranging from 2.5 µg/mL to 1000 µg/mL.

HPLC-UV Method

| HPLC | Shimadzu |
| --- | --- |
| Column | Waters X Bridge, C18, 3.5 µ, 50 * 4.6 mm |
| MP-A | 0.1% Formic acid in Milli Q water |
| MP-B | Acetonitrile—100% |
| Flow Rate | 1.2 mL/min |
| Run time | 5.5 min |
| Injection Volume | 4 µL |

| Gradient Condition | | |
| --- | --- | --- |
| TIME (min) | A (%) | B (%) |
| 0.01 | 95 | 5 |
| 2.50 | 35 | 65 |
| 3.00 | 5 | 95 |
| 4.00 | 5 | 95 |
| 4.50 | 95 | 5 |
| 5.50 | 95 | 5 |

Compound 1 has a thermal solubility of ≥3 mg/mL.
Compound 2 has a thermal solubility of ≥3 mg/mL.
Compound A has a thermal solubility of <0.05 mg/mL.
Compound A, hydrochloride salt has a thermal solubility of <0.05 mg/mL.

Example 7: Kinetic Solubility

Solubility of the compounds was assessed in 10 mM phosphate-buffered saline (PBS) at pH 7 at final concentrations of 20, 40, and 50 mg/mL of test compound.

Experiments with Compound 1 yielded clear solutions at concentrations of 20, 40, and 50 mg/mL after vortex mixing. All solutions remained soluble after storage at 4° C. for 20 hours.

Experiments with Compound 2 yielded milky suspensions at concentrations of 20, 40, and 50 mg/mL after vortex mixing. After sonication in a 40° C. water bath for 30 min, there was no change in appearance. Clear solutions were observed after treatment with 1M HCL (final pH of 4) and 10 seconds of vortexing. Addition of 1M NaOH (final pH of 7) and 10 seconds of vortexing produced clear solutions.

Example 8: Pharmacokinetics (PK)

Stock solutions of test compounds were prepared at 2.5 or 5.0 mg/mL in 10 mM PBS. Male Sprague-Dawley (SD) rats (n=3 per group) or beagle dogs (n=3 per group) were administered test compound by either IV or oral administration. For IV-administered compounds, a three hour infusion was used. For PO-administered compounds, a single bolus dose was used.

After initiation of IV dosing (or after PO bolus dosing), whole blood samples were collected at 1, 3, 3.5, 4, 6, 8, and 24 hour timepoints. All samples were collected into Plasma K2-EDTA collection tubes and processed to separate plasma from red blood cells.

Liquid chromatography-tandem mass spectrometry (LC-MS/MS) was used to analyze all plasma samples, with both the test compound and the active agent Compound A being quantified. The lower limit of quantitation (LLOQ) for both rats and dogs was 1 ng/mL.

Administration of Compound 1 yields a dose-dependent plasma exposures of Compound A after IV or PO administration, demonstrating its utility as a prodrug of Compound A. While concentrations of prodrug Compound 1 show rapid decrease after administration (<100 ng/mL after 4 h for all routes and doses tested in rat, and after 6 h in dog), the released Compound A shows systemic exposure after both oral and IV administration (Tables 2-3).

TABLE 2

Plasma Concentration and Pharamcokinetics of
Compound A After Administration of Compound 1
in Male Sprague-Dawley (SD) Rats (n = 3 per group)

| Dose (mg/kg) of Compound 1 | 37.5 | 75 | 75 |
|---|---|---|---|
| Route of Administration | IV | IV | PO |
| $C_{max}$ (ng/mL) | 9038 | 28492 | 7627 |
| $T_{max}$ (h) | 3 | 3 | 0.67 |
| $T_{1/2}$ (h) | 2.90 | 2.67 | 3.83 |
| $T_{last}$ (h) | 8-24 | 24 | 24 |
| $AUC_{0-last}$ (h * ng/mL) | 31889 | 92792 | 22732 |

TABLE 3

Plasma Concentration and Pharamcokinetics of
Compound A After Administration of
Compound 1 in Beagle Dogs (n = 3 per group)

| Dose (mg/kg) of Compound 1 | 12.5 | 25 | 25 |
|---|---|---|---|
| Route of Administration | IV | IV | PO |
| $C_{max}$ (ng/mL) | 1176 | 2507 | 3350 |
| $T_{max}$ (h) | 3 | 3 | 0.67 |
| $T_{1/2}$ (h) | 4.18 | 3.83 | 5.72 |
| $T_{last}$ (h) | 24 | 24 | 8-24 |
| $AUC_{0-last}$ (h * ng/mL) | 4500 | 8451 | 6184 |

II. Biological Evaluation

Example 9: Treatment of Urinary Tract Infection

Compound A and its prodrugs as disclosed herein were tested in an in vivo mouse model for Urinary Tract Infection. Briefly, mice were infected with *E. coli* UTI 89 to cause a UTI infection and were treated with compounds disclosed herein.

Procedure:

Five days prior to infection, C3H/HeNR female mice were preconditioned with drinking water containing 5% glucose. Mice were rendered unconscious using parenteral anaesthesia (ketamine/medetomidine) then 0.05 mL of a bacterial suspension of *E. coli* UTI 89 ($1.2 \times 10^9$ CFU/mL) ($6.2 \times 10^7$ CFU/mouse) was administered transurethrally into the bladder to cause an ascending UTI infection.

IV or PO treatment was started 24 h post infection with 3, 10, 15 mg/kg/dose IV Compound A; 3, 10, 15.30 mg/kg/dose IV Compound 1; 3, and 10 mg/kg/dose IV Compound 2; and 30 mg/kg/dose oral of either Compound 1 or 2 administered every 12 hours for 3 days (six doses total). Ciprofloxacin was given as a control at 10 mg/kg/dose IV every 12 hours. Compound A was formulated in 10% DMSO, 5% Cremophor, 85% SFI; the remaining compounds used a sterile phosphate-buffered saline (PBS) formulation. Each group was comprised of five mice each.

Urine, bladder, and kidney were harvested at 24 h (pre-treatment group only) and 96 h post infection and quantitatively cultured.

Results

Table 4 and FIG. 1 summarize the results, showing the average terminal burden of *E. coli* UTI 89 in urine, bladder, and kidney at the conclusion of the study (96 hours).

TABLE 4

Terminal Burden of *E. coli* UTI 89 in
Urine, Bladder, and Kidney

| Treatment Group | Urine Terminal Burden (CFU/mL) | Bladder Terminal Burden (CFU/mL) | Kidney Terminal Burden (CFU/mL) |
|---|---|---|---|
| Vehicle IV | $1.73 \times 10^7$ | $3.32 \times 10^8$ | $8.18 \times 10^5$ |
| Vehicle PO | $1.30 \times 10^6$ | $9.59 \times 10^5$ | $2.63 \times 10^5$ |
| Compound A 3 mg/kg/dose IV | $3.03 \times 10^5$ | $2.57 \times 10^5$ | $3.72 \times 10^3$ |
| Compound A 10 mg/kg/dose IV | $6.26 \times 10^4$ | $3.48 \times 10^5$ | $4.44 \times 10^2$ |
| Compound A 15 mg/kg/dose IV | $3.78 \times 10^3$ | $2.62 \times 10^5$ | $1.21 \times 10^2$ |
| Compound 1 3 mg/kg/dose IV | $2.93 \times 10^5$ | $2.64 \times 10^6$ | $4.74 \times 10^4$ |
| Compound 1 10 mg/kg/dose IV | $9.40 \times 10^3$ | $5.05 \times 10^5$ | $5.24 \times 10^2$ |
| Compound 1 15 mg/kg/dose IV | $3.59 \times 10^3$ | $9.57 \times 10^4$ | $1.28 \times 10^2$ |
| Compound 1 30 mg/kg/dose PO | $8.73 \times 10^3$ | $1.81 \times 10^5$ | $4.04 \times 10^2$ |
| Compound 2 3 mg/kg/dose IV | $4.69 \times 10^4$ | $5.15 \times 10^5$ | $2.52 \times 10^3$ |
| Compound 2 10 mg/kg/dose IV | $2.73 \times 10^4$ | $1.17 \times 10^6$ | $9.67 \times 10^2$ |
| Compound 2 30 mg/kg/dose PO | $3.41 \times 10^3$ | $2.82 \times 10^5$ | $3.81 \times 10^2$ |
| Ciprofloxacin 10 mg/kg/dose IV | $5.07 \times 10^2$ | $2.85 \times 10^5$ | $1.88 \times 10^2$ |

Treatment with Compound A, Compound 1, and Compound 2 resulted in statistically significant reductions in bacterial burden in urine relative to vehicle-treated controls. There was no significant difference in efficacy between equivalent doses of Compound A, Compound 1, and Compound 2 administered by IV administration.

Treatment with Compound A, Compound 1, and Compound 2 by IV administration resulted in reductions in bacterial burden in bladder relative to the vehicle-treated controls.

Treatment with Compound A, Compound 1, and Compound 2 by IV administration resulted in statistically significant reductions in bacterial burden in kidney relative to the vehicle-treated control. PO administration of Compound 1 and Compound 2 was also efficacious. There was no significant difference in efficacy between equivalent doses of Compound A, Compound 1, and Compound 2 administered by IV administration.

Figure 2:
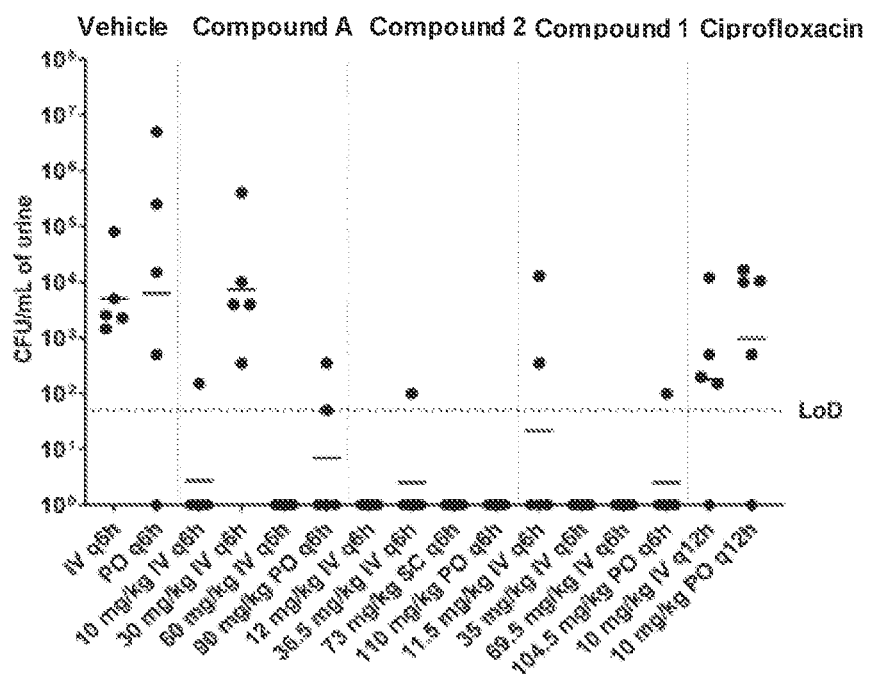
FIG. 2 shows the average terminal burden of *K. pneumoniae* BAA-1705 in urine, bladder, and kidney at the conclusion of a 96 h urinary tract infection study.
Figure 2:
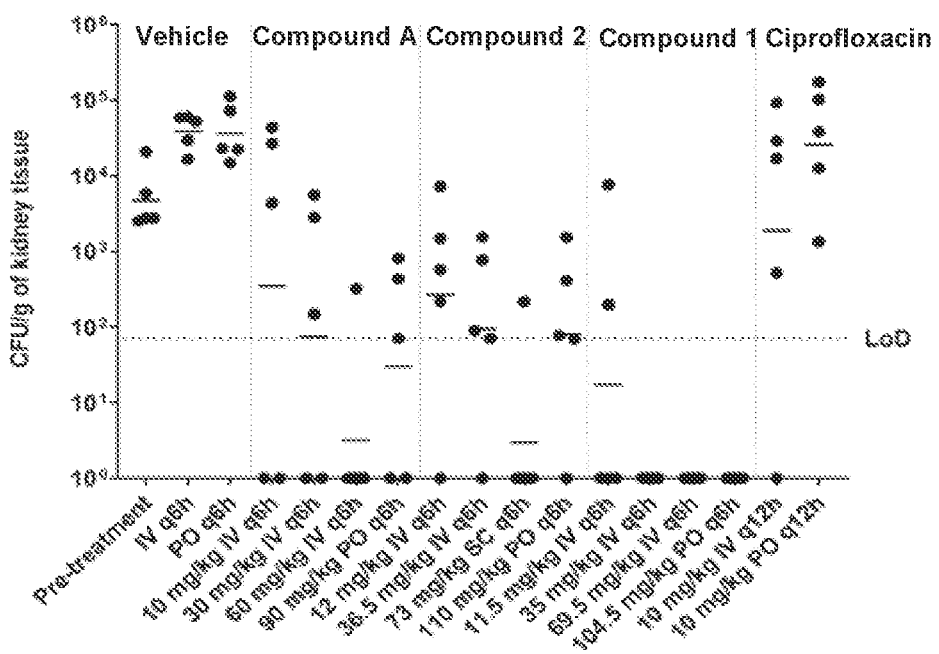

The experiment was repeated using *K. pneumoniae* BAA-1705 (MDR; $MIC_{90}$ strain). Table 5 and FIG. 2 summarize the results, showing the average terminal burden of *K. pneumoniae* BAA-1705 in urine, bladder, and kidney at the conclusion of the study (96 hours).

TABLE 5

Terminal Burden of *K. pneumoniae* BAA-1705 in Urine, Bladder, and Kidney

| Treatment Group | Urine Terminal Burden (CFU/mL) | Bladder Terminal Burden (CFU/mL) | Kidney Terminal Burden (CFU/mL) |
|---|---|---|---|
| Vehicle IV | $5.09 \times 10^3$ | $4.58 \times 10^0$ | $3.92 \times 10^4$ |
| Vehicle PO | $6.23 \times 10^3$ | $2.76 \times 10^1$ | $3.63 \times 10^4$ |
| Compound A 10 mg/kg/dose IV | $2.72 \times 10^0$ | $9.29 \times 10^1$ | $3.47 \times 10^2$ |
| Compound A 30 mg/kg/dose IV | $7.41 \times 10^3$ | BLoD | $7.48 \times 10^1$ |
| Compound A 60 mg/kg/dose IV | BLoD | BLoD | $3.17 \times 10^0$ |
| Compound A 90 mg/kg/dose PO | $7.06 \times 10^0$ | BLoD | $3.01 \times 10^1$ |
| Compound 1 11.5 mg/kg/dose IV | $2.15 \times 10^1$ | BLoD | $1.72 \times 10^1$ |
| Compound 1 35 mg/kg/dose IV | BLoD | BLoD | BLoD |
| Compound 1 69.5 mg/kg/dose IV | BLoD | $4.58 \times 10^0$ | BLoD |
| Compound 1 104.5 mg/kg/dose PO | $2.51 \times 10^0$ | BLoD | BLoD |
| Ciprofloxacin 10 mg/kg/dose IV | $1.78 \times 10^2$ | $2.27 \times 10^1$ | $1.88 \times 10^3$ |
| Ciprofloxacin 10 mg/kg/dose PO | $9.71 \times 10^2$ | $4.05 \times 10^2$ | $2.59 \times 10^4$ |

BLoD = below limit of detection

Treatment with Compound A, Compound 1, and Compound 2 resulted in statistically significant reductions in bacterial burden in urine relative to vehicle-treated controls and the ciprofloxacin control (except for the 30 mg/kg IV Compound A experiment).

Treatment with Compound A, Compound 1, and Compound 2 resulted in statistically significant reductions in bacterial burden in kidney relative to vehicle-treated controls and the ciprofloxacin control. Furthermore, treatment with Compound 1 resulted in bacterial loads below the limit of detection for all routes of administration.

III. Pharmaceutical Compositions

Example A-1: Parenteral Pharmaceutical Composition

To prepare a parenteral pharmaceutical composition suitable for administration by injection (subcutaneous, intravenous), 1-100 mg of a compound Formula (I), or a pharmaceutically acceptable salt, or a pharmaceutally acceptable solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of a compound of Formula (I), or a pharmaceutically acceptable salt, or a pharmaceutally acceptable solvate thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound of Formula (I), or a pharmaceutically acceptable salt, or a pharmaceutically acceptable solvate thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound of Formula (I), or a pharmaceutically acceptable salt, or a pharmaceutically acceptable solvate thereof, is mixed with starch or other suitable powder blend. The mixture is incorporated into an oral dosage unit such as a hard gelatin capsule, which is suitable for oral administration.

In another embodiment, 10-500 mg of a compound of Formula (I), or a pharmaceutically acceptable salt thereof, is placed into Size 4 capsule, or size 1 capsule (hypromellose or hard gelatin) and the capsule is closed.

The examples and embodiments described herein are for illustrative purposes only and various modifications or changes suggested to persons skilled in the art are to be included within the spirit and purview of this application and scope of the appended claims.

What is claimed is:

1. A compound having the structure:

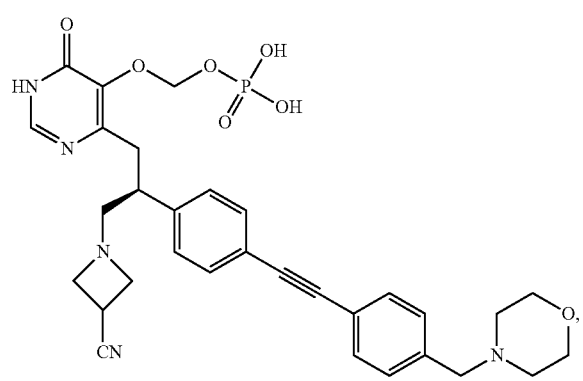 [SMILES: N#CC1CN(C[C@@H](Cc2nc[nH]c(=O)c2OCOP(=O)(O)O)c2ccc(C#Cc3ccc(CN4CCOCC4)cc3)cc2)C1]

or a pharmaceutically acceptable salt, or a solvate thereof.

2. A pharmaceutical composition comprising the compound of claim 1, or a pharmaceutically acceptable salt, or a solvate thereof, and at least one pharmaceutically acceptable excipient.

3. A method of treating a gram-negative bacterial infection in a patient in need thereof comprising administering to the patient the compound of claim 1, or a pharmaceutically acceptable salt, or a solvate thereof, wherein the gram-negative bacterial infection is selected from chronic urinary tract infection, complicated urinary tract infection, cystitis, pyelonephritis, urethritis, recurrent urinary tract infection, bladder infection, urethral infection, and kidney infection.

4. The method of claim 3, wherein the gram-negative bacterial infection is chronic urinary tract infection or complicated urinary tract infection.

\* \* \* \* \*